(12) United States Patent
Goepfert et al.

(10) Patent No.: US 7,892,790 B2
(45) Date of Patent: Feb. 22, 2011

(54) PROTEIN EXPRESSION IN RODENT CELLS

(75) Inventors: Ulrich Goepfert, Munich (DE); Erhard Kopetzki, Penzberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/083,535

(22) PCT Filed: Oct. 26, 2006

(86) PCT No.: PCT/EP2006/010308

§ 371 (c)(1),
(2), (4) Date: Apr. 14, 2008

(87) PCT Pub. No.: WO2007/048601

PCT Pub. Date: May 3, 2007

(65) Prior Publication Data

US 2010/0021965 A1  Jan. 28, 2010

(30) Foreign Application Priority Data

Oct. 28, 2005 (EP) .................................. 05023611

(51) Int. Cl.
  C12P 21/06  (2006.01)
  C12N 5/10  (2006.01)
(52) U.S. Cl. ...................... 435/69.1; 435/358
(58) Field of Classification Search ............... 435/69.1, 435/358
See application file for complete search history.

(56) References Cited

U.S. PATENT DOCUMENTS

| 4,686,186 A | 8/1987 | Sugden |
| 5,707,830 A | 1/1998 | Calos |
| 5,976,807 A | 11/1999 | Horlick et al. |
| 2005/0227317 A1* | 10/2005 | Kunaparaju et al. ........ 435/69.1 |

FOREIGN PATENT DOCUMENTS

| WO | WO 02/27005 | 4/2002 |
| WO | WO 02/090533 | 11/2002 |
| WO | WO 2004/018506 | 3/2004 |
| WO | WO 2004/053137 | 6/2004 |
| WO | WO 2005/024030 | 3/2005 |

OTHER PUBLICATIONS

Kunaparaju et al. (published online Jun. 9, 2005; Epi-CHO, an episomal expression system for recombinant protein production in CHO cells. Biotechnology and Bioengineering 91(6): 670-677).*
pCEP4 map, Invitrogen Life Technologies, 2010.*
pREP10 map, Invitrogen Life Technologies, 2010.*
Aiyar, A. et al, *Embo J.*, 17 (1998) 6394-6403.
Gorman et al, *Proc. Natl. Acad. Sci.*, 79 (1982) 6777-6781.
Horlick, R.A. et al, *Prot. Exp. Purif.* 9 (1997) 301-308.
Krysan, P.J. et al, *Mol. Cell. Biol* 9 (1989) 1026-1033.
Wysokenski, D.A. et al, *J. Vir.* 63 (1989) 2657-26666.
Yates, J.L. et al, *J. Vir,* 74 (2000) 4512-4522.
Yates, J.L. et al, *Nature* (London) 313 (1985) 812-815.
Yates, J.L., in *DNA Replication in Eukaryotic Cells* ed. by DePhamphilis, M.L., Cold Spring Harbor Laboratory, NY (1996) 751-774.
Mizuguchi, H. et al, *FEBS Letters*, 472 (2000) 173-178.
Tomiyasu, K.I. et al, *Biochem. Biophys. Res. Commun.*, 253 (1998) 733-738.
Bendig, M.M., *Genetic Engineering*, 7 (1988) 91-127.
Boshart et al, *Cell* 41 (1985) 521-530.
Hung, S.C. et al, *PNAS*, 98 (2001) 1865-1870.

* cited by examiner

*Primary Examiner*—Karen Cochrane Carlson
(74) *Attorney, Agent, or Firm*—George W. Johnston; Dennis P. Tramaloni

(57) ABSTRACT

A method is described for the expression of heterologous polypeptides in rodent cells. The method comprises the oriP/EBNA-1 episomal replication and maintenance system of the Epstein-Barr-Virus (EBV). With the stable integration of an EBNA-1-protein expression cassette under the control of a promoter into the genome of a rodent cell an EBNA-1-protein expression in the cells was obtained. The heterologous protein is expressed from an episome comprising an EBV origin of replication and a functional expression cassette of said heterologous protein. The invention further comprises transformed rodent cell lines, a method for the production of a heterologous protein in said cell lines and a kit for the construction of said cell lines.

13 Claims, 6 Drawing Sheets

A

B a)

b)

a)

b)

PROTEIN EXPRESSION IN RODENT CELLS

The current invention relates to the expression of heterologous proteins in rodent cells. The protein encoding nucleic acid is provided on an episome under the control and maintenance of the oriP/EBNA-1-system of the Epstein-Barr-Virus wherein both oriP and the structural gene for EBNA-1 are located on different elements inside the cell.

TECHNOLOGICAL BACKGROUND

The role and impact of biotechnological production processes gained weight during the last years. Concurrently with the rising importance of biotechnological processes the complexity of the manufactured products steadily increases.

Possible host cells for the expression of heterologous proteins are HEK (Human Embryonal Kidney), HeLa (Henrietta Lacks), COS (SV40 transformed African Green Monkey kidney cells) and CHO (Chinese Hamster Ovary) cells, because heterologous proteins expressed in these hosts can be folded, processed, maturated by proteases, glycosylated, and sulfated according to the pattern in human cells (see e.g. Watson, E., et al., Glycobiol. 4 (1994) 227-37).

The Epstein-Barr-Virus (EBV) is a pathogen of human B lymphocytes. It belongs to the class of human herpes viruses (herpesviridae). B lymphocytes transformed by EBV may propagate unregulatedly (Miller, G., in Virology ed. by Fields, B., Raven Press, N.Y. (1985) 563-590). A characteristic feature of EBV-transformed cells is the expression of the so called Epstein-Barr-Virus-Nuclear-Antigen (EBNA) proteins. Of these, six different variants have been identified so far.

The EBNA-1 protein plays an important role in the replication cycle of the EBV nucleic acid in transformed cells. In combination with a second EBV element, the origin of replication (oriP), which acts in cis, the replication and maintenance of episomes within the cell is enabled (Lupton, S., and Levine, A. J., Mol. Cell. Biol. 5 (1985) 2533-2542; Yates, J. L., et al., Nature (London) 313 (1985) 812-815).

The oriP-segment is made up of two regions: the dyad symmetry element and the family of repeats. The first is a 65 bp sequence segment. It is separated in the virus' nucleic acid by circa 1000 bp from the family of repeats. This second segment is composed of a 30 bp sequence that is repeated 20 times (Hudson, G. S., et al., Virology 147 (1985) 81-98; Reisman, D., et al., Mol. Cell. Biol. 5 (1985) 1822-1832).

The 30-bp family of repeats possesses the ability to enhance transcription, whereas the dyad symmetry element plays a role in replication. The complete oriP-segment assists in maintaining the plasmid extrachromosomally.

The combination of the EBNA-1 protein, i.e. a trans-acting initiator protein, and oriP permits the construction of plasmids, which, once they have been introduced into a cell, are stably maintained as episomes and are stably replicated during cell proliferation (see e.g. Yates, J. L., et al., Nature (London) 313 (1985) 812-815; Reisman, D., et al., Mol. Cell. Biol. 5 (1985) 1822-1832). These two elements exploit the replication mechanism of the host cell for replication of the episome (Bode, J., et al., Gene Ther. Mol. Biol. 6 (2001) 33-46).

Krysan, P. J., et al. (Mol. Cell. Biol. 9 (1989) 1026-1033) demonstrated that plasmids comprising the family of repeats of the EBV origin of replication can be permanently retained in the cell nucleus of human cells. Therefore the presence of the EBNA-1 protein was sufficient; no other element of the EBV was required (see also Aiyar, A., et al., EMBO J. 17 (1998) 6394-6403; Hung, S. C., et al., PNAS 98 (2001) 1865-1870; Yates, J. L., in DNA Replication in Eukaryotic Cells, ed. by DePhamphilis, M. L., Cold Spring Harbor Laboratory, N.Y. (1996) pages 751-774; Yates, J. L., et al., J. Vir. 74 (2000) 4512-4522).

The EBNA-1 protein links the episome to the host cell's chromosome during episome replication and thereby assures the propagation of the episome during cell division.

Such a mutual relationship is also known for other viruses, e.g. the large T-antigen from the Simian Virus 40 (SV 40) and the E1/E2-proteins from the Bovine Papilloma Virus (BPV) (see e.g. Gilbert, D. M., et al., Cell 50 (1987) 59-68; DuBridge, R. B., et al., Mutagen. 3 (1988) 1-9; Lebkowski, J. S., et al., Mol. Cell. Biol. 4 (1984) 1951-1960).

The combination of the elements EBNA-1 and oriP of the EBV has been used for the preparation of not integrating, extrachromosomal, autonomously replicating episomes. Horlick et al., e.g., used HEK (Human Embryonic Kidney) cells stably expressing the EBNA-1 protein for the expression of CRHR (corticotrophin releasing hormone receptor) from a plasmid containing the EBV oriP (Horlick, R. A., et al., Prot. Exp. Purif. 9 (1997) 301-308).

In U.S. Pat. No. 4,686,186 a recombinant vectors and a eukaryotic host transformed thereby have been reported. The EBV elements oriP and EBNA-1 were combined on the recombinant vector.

In WO 2002/090533 a process for the production of recombinant proteins by transient transfection of suspension-grown human embryonic kidney cells (293 cell line and its genetic variants) is reported. Plasmids providing the EBV origin of replication are maintained extrachromosomally.

In WO 2004/053137 a method for the production of recombinant polypeptides and/or untranslated RNA molecules in host cells is reported. WO 2004/018506 reports compositions and methods applicable in a regulatable expression system that is transiently transfected into mammalian host cells.

US patent application 2002/0086419 reports a recombinant vector for stable persistence of exogenous DNA in eukaryotic host cells and the uses of the recombinant vector for long-term stable production of a gene product in the host cell.

An expression vector useful for transfection of a selected mammalian host cell is reported in U.S. Pat. No. 5,707,830. The expression vector contains an Epstein-Barr-Virus family of repeats, a copy of the EBNA-1 gene that can be functionally expressed in the host cell, a eukaryotic DNA fragment, which provides the ability of the vector to replicate in the host cell, and an expression cassette.

WO 2002/027005 reports an enhanced transfection system comprising an episomal maintenance system, a strong promoter/enhancer, a protein transactivation system and a DNA coding for a heterologous protein. The preferred cell lines should be non-rodent, because an oriP containing plasmid is not replicating efficiently and CHO cells, e.g., lack cellular factors for the transactivation system.

Wysokenski, D. A., and Yates, J. L., (J. Vir. 63 (1989) 2657-2666) mentioned that EBV plasmid replication does not cross species lines from cells of primates to cells of rodents. This is based on a missing interaction with a host protein involved in DNA replication, which is missing in rodents.

Tomiyasu, K.-i., et al., Biochem. Biophys. Res. Commun. 253 (1998) 733-738, Mizuguchi, H., et al., FEBS Letters 472 (2000) 173-178, and WO 2005/024030 report plasmids containing both an oriP and EBNA-1 structural gene together with other elements.

U.S. Pat. No. 5,976,807 reports a method for producing recombinant eukaryotic cell lines expressing multiple proteins of interest. Transfected cells are obtained expressing an EBNA-1 protein and contain at least two transfected episomes.

SUMMARY OF THE INVENTION

The current invention provides an expression system for the expression of heterologous proteins in rodent cell lines. This system comprises the oriP/EBNA-1 episomal replication and maintenance system of the Epstein-Barr-Virus.

Specifically, the invention provides a rodent cell, wherein the rodent cell expresses the Epstein Barr Virus Nuclear Antigen 1 (EBNA-1) and contains an episome, wherein said episome comprises a) a prokaryotic origin of replication;
b) a selection marker;
c) an Epstein-Barr-Virus (EBV) origin of replication (oriP);
d) an expression cassette suitable for the expression of a heterologous polypeptide in said rodent cell, whereby said expression cassette comprises a promoter sequence, a 5' untranslated region, a nucleic acid sequence encoding said heterologous protein, and a 3' untranslated region comprising a polyadenylation signal.

The current invention further provides a method for obtaining a rodent cell according to the invention, whereby the method comprises the steps of a) providing a rodent cell;
b) providing a plasmid comprising a prokaryotic origin of replication, a selection marker, and a functional expression cassette for the Epstein Barr Virus Nuclear Antigen 1 (EBNA-1), whereby said expression cassette comprises a promoter sequence, a 5' untranslated region, a nucleic acid sequence encoding the EBNA-1-protein, and a 3' untranslated region comprising a polyadenylation signal;
c) introducing said plasmid b) into said rodent cell a);
d) selecting a stably transformed rodent cell;
e) providing one or more further plasmid comprising a prokaryotic origin of replication, a selection marker, an Epstein Barr Virus (EBV) origin of replication (oriP), and an expression cassette suitable for the expression of a heterologous protein in the transformed rodent cell, whereby said expression cassette comprises a promoter sequence, a 5' untranslated region, a nucleic acid sequence encoding the heterologous polypeptide, and a 3' untranslated region comprising a polyadenylation signal,
f) introducing said further plasmid e) into rodent cell d);
g) repeating steps e) to f) for up to 5 times.

The current invention further provides a process for the production of a heterologous polypeptide, wherein said process comprises a) providing a rodent cell according to the invention;
b) culturing the rodent cell under conditions suitable for the expression of the heterologous polypeptide;
c) recovering the heterologous polypeptide from the culture.

The current invention also provides a kit for the production of a rodent cell according to the invention, wherein said kit comprises a) a rodent cell;
b) a first plasmid comprising a prokaryotic origin of replication, a selection marker, and a functional expression cassette for the Epstein Barr Virus Nuclear Antigen 1 (EBNA-1), whereby said expression cassette comprises a promoter sequence, a 5' untranslated region, a nucleic acid sequence encoding the EBNA-1 protein, and a 3' untranslated region comprising a polyadenylation signal;
c) a second plasmid comprising a prokaryotic origin of replication, a selection marker, an Epstein Barr Virus (EBV) origin of replication (oriP), and an expression cassette suitable for the expression of a heterologous polypeptide in the rodent cell, whereby the expression cassette comprises a promoter sequence, a cloning site for the introduction of a nucleic acid sequence, and a 3' untranslated region comprising a polyadenylation signal.

In one embodiment of the invention the rodent cell is a CHO cell.

In another embodiment of the invention the CHO cell is selected from the group comprising the cells CHO-K1, CHO-DXB11, CHO-DG44, and CHO cells expressing the EBNA-1 protein.

In another embodiment of the current invention the heterologous polypeptide to be expressed is selected from the group comprising prodrugs, enzymes, enzyme fragments, enzyme inhibitors, enzyme activators, biologically active polypeptides, hedgehog proteins, bone morphogenetic proteins, growth factors, erythropoietin, thrombopoietin, G-CSF, interleukins, interferons, immunoglobulins, or immunoglobulin fragments.

In one embodiment said heterologous polypeptide is an immunoglobulin or an immunoglobulin fragment.

In another embodiment the production of the heterologous protein according to the current invention is carried out under transient transfection.

In another embodiment said heterologous polypeptide is secreted into the culture medium.

In a further embodiment of the invention the plasmid introduced into the rodent cell contains at least two selection markers, preferably at least one prokaryotic selection marker and at least one eukaryotic selection marker.

In a further embodiment of the invention the number of plasmids introduced into one rodent cell is between one and five plasmids.

In another embodiment of the invention is the number of plasmids introduced into the rodent cell in the same step between one and three, preferably between one and two plasmids.

DETAILED DESCRIPTION OF THE INVENTION

The current invention provides a rodent cell, wherein said rodent cell expresses the Epstein Barr Virus Nuclear Antigen 1 (EBNA-1) and contains an episome, wherein said episome comprises a) a prokaryotic origin of replication;
b) a selection marker;
c) an Epstein-Barr-Virus (EBV) origin of replication (oriP);
d) an expression cassette suitable for the expression of a heterologous polypeptide in said rodent cell, whereby said expression cassette comprises a promoter sequence, a 5' untranslated region, a nucleic acid sequence encoding said heterologous polypeptide, and a 3' untranslated region comprising a polyadenylation signal.

Useful methods and techniques for carrying out the current invention are described in e.g. Ausubel, F. M., ed., Current Protocols in Molecular Biology, Volumes I to III (1997); Glover, N. D., and Hames, B. D., ed., DNA Cloning: A Practical Approach, Volumes I and II (1995), Oxford University Press; Freshney, R. I. (ed.), Animal Cell Culture—a practical approach, IRL Press (1986); Watson, J. D., et al., Recombinant DNA, Second Edition, CHSL Press (1992); Winnacker, E. L., From Genes to Clones; N.Y., VCH Publishers (1987); Celis, J., ed., Cell Biology, Second Edition, Academic Press (1998); Freshney, R. I., Culture of Animal Cells: A Manual of Basic Techniques, Second Edition, Alan R. Liss, Inc., N.Y. (1987).

A "nucleic acid" as used herein, refers to an at least partially non-naturally occurring nucleic acid encoding a polypeptide which can be produced recombinantly. "Non-naturally occurring" may refer either to the sequences of the individual nucleotides or to the combination of employed functional elements, which is not limited to promoter, 3' untranslated region, enhancer, or origin of replication. The nucleic acid can be build up of nucleic acid fragments, preferably DNA-fragments, which are either isolated or synthesized by chemical means. The nucleic acid can be integrated into another nucleic acid, e.g. in a plasmid or the genome/chromosome of a eukaryotic host cell. Plasmid includes among others shuttle and expression vectors. Typically, a plasmid will also comprise a prokaryotic propagation unit comprising an origin of replication (e.g. the ColE1 origin of replication) and a selectable marker (e.g. ampicillin or tetracycline resistance gene), for replication and selection, respectively, of the vector in bacteria.

A nucleic acid is likewise characterized by its nucleic acid sequence consisting of individual nucleotides.

The term "nucleic acid sequence" as used within this application denotes the nucleotide sequences of a nucleic acid molecule and variants thereof, which code for a peptide, polypeptide or protein or a functional variant thereof, i.e. e.g. proteins with different amino acid sequences but having the same biological functionality/activity. These modifications are due e.g. to the degeneration of the genetic code, mutations, such as point mutations, deletions, insertions and the like. A variant of a protein differs in the amino acid sequence from a parent protein's amino acid sequence by virtue of addition, deletion and/or substitution of one or more amino acid residue(s) in the parent protein sequence. Ordinarily, a variant will have an amino acid sequence having at least 90% amino acid sequence identity with the parent protein sequence, more preferably at least 95%, and most preferably at least 99%.

An "expression cassette" refers to a nucleic acid sequence that comprises the elements necessary for expression and secretion of at least the contained structural gene in a cell.

A "gene" denotes a segment, e.g. on a chromosome or on a plasmid, which is necessary for the expression of a peptide, polypeptide or protein. Beside the coding region the gene comprises other functional elements including a promoter, introns, and terminators.

A "structural gene" denotes the coding region of a gene without a signal sequence.

The term "promoter" as used within this application denotes a regulatory nucleic acid sequence used to push the transcription of a downstream nucleic acid sequence. The promoter sequence can be selected from the group comprising the promoter sequences of cytomegalovirus (CMV), early and late simian virus 40 (SV40) (Bernoist, C., and Chambon, P., Nature 290 (1981) 304-10), the promoter contained in the 3' long terminal repeat of Rous Sarcoma Virus (RSV) (Yamamoto et al., Cell 22:787-97 (1980)), glycerin aldehyde phosphate dehydrogenase (GADPH), retroviral LTRs, elongation factor 1 alpha (EF-1 alpha), ubiquitin, Herpes simplex virus thymidine kinase (HSVTK) (see also e.g. Lee, A., et al., Mol. Cell. 7 (1997) 495-501, Wagner et al., Proc. Natl. Acad. Sci. U.S.A. 78:1441-45 (1981)), and the regulatory sequences of the metallothionein gene (Brinster et al., Nature 296 (1982) 39-42), and the like. Preferred are strong promoter, such as adenoviral promoters (e.g. adenoviral major late promoter), albumin promoter, ApoAl promoter, beta-actin promoter, heat shock promoters, heterologous promoters (e.g. CMV), human globin and growth hormone promoters, inducible promoters (e.g. MMT), retroviral LTR promoters, RSV, as well as thymidine kinase promoters (e.g. Herpes Simplex thymidine kinase promoter). Especially preferred are strong viral promoters, such as adenoviral promoters, immediate early and late cytomegalovirus promoter (CMV; Boshart et al., Cell 41 (1985) 521-30), mouse mammary tumor virus promoter (MMTV), and Rous sarcoma virus promoter from the long terminal repeats (LTR-RSV; Gorman et al., Proc. Natl. Acad. Sci. USA 79 (1982) 6777-81).

The term "polyadenylation signal" as used within this application denotes a nucleic acid sequence used to induce cleavage and polyadenylation of primary transcripts of a specific nucleic acid sequence segment. The 3' untranslated region comprising a polyadenylation signal can be selected from the group consisting of the 3' untranslated region comprising a polyadenylation signals derived from SV40, the gene for bovine growth hormone (BGH), immunoglobulin genes, and the thymidine kinase gene (tk, e.g. Herpes Simplex thymidine kinase polyadenylation signal).

A "resistance gene" or a "selection marker", which is used interchangeably within this application, is a gene that allows cells carrying the gene to be specifically selected for or against, in the presence of a corresponding selection agent. A useful positive resistance gene is an antibiotic resistance gene. This selection marker allows the host cell transformed with the gene to be positively selected for in the presence of the corresponding antibiotic; a non-transformed host cell would not be capable to grow or survive under the selective culture conditions. Selection markers can be positive, negative or bifunctional. Positive selection markers allow selection for cells carrying the marker, whereas negative selection markers allow cells carrying the marker to be selectively eliminated. Typically, a selection marker will confer resistance to a drug or compensate for a metabolic or catabolic defect in the host cell. In procaryotic cells, amongst others, genes conferring resistance against ampicillin, tetracycline, kanamycin or chloramphenicol are frequently used. Resistance genes useful with eukaryotic cells include, e.g., the genes for aminoglycoside phosphotransferase (APH), such as the hygromycin phosphotransferase (hyg), neomycin and G418 APH, dihydrofolate reductase (DHFR), thymidine kinase (tk), glutamine synthetase (GS), asparagine synthetase, tryptophan synthetase (indole), histidinol dehydrogenase (histidinol D), and genes encoding resistance to puromycin, bleomycin, phleomycin, chloramphenicol, Zeocin, and mycophenolic acid. Further marker genes are described in WO 92/08796 and WO 94/28143.

Beside a selection in the presence of a corresponding selection agent a selection marker can also provide a gene encoding a molecule normally not present in the cell, e.g. green fluorescent protein (GFP). Cells harboring such a gene encoding GFP can easily be distinguished from cells not harboring this gene, only by the detection of the fluorescence emitted by the GFP.

Eukaryotic expression vectors/plasmids can be propagated in prokaryotic cells. Therefore a eukaryotic expression vector/plasmid may and often will carry more than one resistance gene, i.e. one resistance gene usable for prokaryotic selection and one usable for eukaryotic selection.

"Regulatory elements" as used herein, refer to nucleotide sequences present in cis, necessary for transcription and/or translation of the structural gene encoding a peptide, polypeptide, or protein of interest. The transcriptional regulatory elements normally comprise a promoter upstream of the structural gene to be expressed, transcriptional initiation and termination sites, and a polyadenylation signal sequence. The term "transcriptional initiation site" refers to the nucleic acid base in the gene corresponding to the first nucleic acid incorporated into the primary transcript, i.e. the mRNA precursor; the transcriptional initiation site may overlap with the promoter sequence. The term "transcriptional termination site" refers to a nucleotide sequence normally represented at the 3' end of a gene of interest to be transcribed, that causes RNA polymerase to terminate transcription. The polyadenylation signal sequence, or polyA addition signal, provides the signal for the cleavage at a specific site at the 3' end of eukaryotic mRNA and the post-transcriptional addition in the nucleus of a sequence of about 100-200 adenine nucleotides (polyA tail) to the cleaved 3' end. The polyadenylation signal sequence may include the consensus sequence AATAAA located at about 10-30 nucleotides upstream from the site of cleavage.

To produce a secreted polypeptide, the structural gene of interest additionally comprises a DNA segment that encodes a signal sequence/leader peptide. The signal sequence directs the newly synthesized peptide, polypeptide, or protein to and through the ER membrane where the polypeptide can be routed for secretion. The signal sequence is cleaved off by signal peptidases during the passage of the protein through the ER membrane. As for the function of the signal sequence the recognition by the host cell's secretion machinery is essential. Therefore the used signal sequence has to be recognized by the host cell's proteins and enzymes of the secretion machinery.

Translational regulatory elements include a translational initiation (AUG) and stop codon (TAA, TAG or TGA). An internal ribosome entry site (IRES) can be included in some constructs.

A "promoter" refers to a polynucleotide sequence that controls transcription of a gene/structural gene or nucleic acid sequence to which it is operably linked. A promoter includes signals for RNA polymerase binding and transcription initiation. The promoters used will be functional in the cell type of the host cell in which expression of the selected sequence is contemplated. A large number of promoters including constitutive, inducible and repressible promoters from a variety of different sources, are well known in the art (and identified in databases such as GenBank) and are available as or within cloned polynucleotides (from, e.g., depositories such as ATCC as well as other commercial or individual sources). A "promoter" comprises a nucleotide sequence that directs the transcription of a structural gene. Typically, a promoter is located in the upstream region (5') of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee, R. E., et al., Mol. Endocrinol. 7 (1993) 551-60), cyclic AMP response elements (CREs), serum response elements (SREs; Treisman, R., Seminars in Cancer Biol. 1 (1990) 47-58), glucocorticoid response elements (GREs), and binding sites for other transcription factors, such as CRE/ATF (O'Reilly, M. A., et al., J. Biol. Chem. 267 (1992) 19938-43), AP2 (Ye, J., et al., J. Biol. Chem. 269 (1994) 25728), SP1, cAMP response element binding protein (CREB; Loeken, M. R., Gene Expr. 3 (1993) 253-64) and octamer factors (see, in general, Watson et al., eds., Molecular Biology of the Gene, 4th ed., The Benjamin/Cummings Publishing Company, Inc. 1987, and Lemaigre, F. P. and Rousseau, G. G., Biochem. J. 303 (1994) 1-14). If a promoter is an inducible promoter, then the rate of transcription increases in response to an inducing agent. In contrast, the rate of transcription is not regulated by an inducing agent if the promoter is a constitutive promoter. Repressible promoters are also known. For example, the c-fos promoter is specifically activated upon binding of growth hormone to its receptor on the cell surface. Tetracycline (tet) regulated expression can be achieved by artificial hybrid promoters that consist e.g. of a CMV promoter followed by two Tet-operator sites. The Tet-repressor binds to the two Tet-operator sites and blocks transcription. Upon addition of the inducer tetracycline, Tet-repressor is released from the Tet-operator sites and transcription proceeds (Gossen, M. and Bujard, H. PNAS 89 (1992) 5547-5551). For other inducible promoters including metallothionein and heat shock promoters, see, e.g., Sambrook et al. (supra) and Gossen, M., et al., Curr. Opin. Biotech. 5 (1994) 516-520. Among the eukaryotic promoters that have been identified as strong promoters for high-level expression are the SV40 early promoter, adenovirus major late promoter, mouse metallothionein-I promoter, Rous sarcoma virus long terminal repeat, Chinese hamster elongation factor 1 alpha (CHEF-1, see e.g. U.S. Pat. No. 5,888,809), human EF-1 alpha, ubiquitin, and human cytomegalovirus immediate early promoter (CMV IE).

The "promoter" can be constitutive or inducible. An enhancer (i.e., a cis-acting DNA element that acts on a promoter to increase transcription) may be necessary to function in conjunction with the promoter to increase the level of expression obtained with a promoter alone, and may be included as a transcriptional regulatory element. Often, the polynucleotide segment containing the promoter will include enhancer sequences as well (e.g., CMV or SV40).

An "enhancer", as used herein, refers to a polynucleotide sequence that enhances transcription of a gene or coding sequence to which it is operably linked. Unlike promoters, enhancers are relatively orientation and position independent and have been found 5' or 3' (Lusky, M., et al., Mol. Cell. Bio., 3 (1983) 1108-22) to the transcription unit, within an intron (Banerji, J., et al., Cell, 33 (1983) 729-40) as well as within the coding sequence itself (Osborne, T. F., et al., Mol. Cell. Bio., 4 (1984) 1293-305). Therefore, enhancers may be placed upstream or downstream from the transcription initiation site or at considerable distances from the promoter, although in practice enhancers may overlap physically and functionally with promoters. A large number of enhancers, from a variety of different sources are well known in the art (and identified in databases such as GenBank) and available as or within cloned polynucleotide sequences (from, e.g., depositories such as the ATCC as well as other commercial or individual sources). A number of polynucleotides comprising promoter sequences (such as the commonly-used CMV promoter) also comprise enhancer sequences. For example, all of the strong promoters listed above may also contain strong enhancers (see e.g. Bendig, M. M., Genetic Engineering, 7 (1988) 91-127).

"Operably linked" refers to a juxtaposition of two or more components, wherein the components so described are in a relationship permitting them to function in their intended manner. For example, a promoter and/or enhancer are operably linked to a coding sequence, if it acts in cis to control or modulate the transcription of the linked sequence. Generally, but not necessarily, the DNA sequences that are "operably linked" are contiguous and, where necessary to join two protein encoding regions such as a secretory leader and a polypeptide, contiguous and in reading frame. However, although an operably linked promoter is generally located upstream of the coding sequence, it is not necessarily contiguous with it. Enhancers do not have to be contiguous. An enhancer is operably linked to a coding sequence if the enhancer increases transcription of the coding sequence. Operably linked enhancers can be located upstream, within or downstream of coding sequences and at considerable distance from the promoter. A polyadenylation site is operably linked to a coding sequence/structural gene if it is located at the downstream end of the coding sequence such that transcription proceeds through the coding sequence into the polyadenylation sequence. Linking is accomplished by recombinant methods known in the art, e.g., using PCR methodology and/or by ligation at convenient restriction sites. If convenient restriction sites do not exist, then synthetic oligonucleotide adaptors or linkers are used in accord with conventional practice.

The term "expression" as used herein refers to transcription and/or translation occurring within a host cell. The level of transcription of a desired product in a host cell can be determined on the basis of the amount of corresponding mRNA that is present in the cell. For example, mRNA transcribed from a selected sequence can be quantitated by PCR or by Northern hybridization (see Sambrook et al., Molecular Cloning: A Laboratory Manual, Cold Spring Harbor Laboratory Press, New York (1989)). Protein encoded by a selected sequence can be quantitated by various methods, e.g. by ELISA, by assaying for the biological activity of the protein, or by employing assays that are independent of such activity, such as Western blotting or radioimmunoassay, using antibodies that recognize and bind to the protein (see Sambrook et al., 1989, supra).

A "host cell" refers to a cell into which the gene encoding the polypeptide of the invention is introduced. Host cell includes both prokaryotic cells used for propagation of the plasmids/vectors, and eukaryotic cells for expression of the structural gene. Typically, the eukaryotic cells are mammalian cells.

A "polypeptide" is a polymer of amino acid residues joined by peptide bonds, whether produced naturally or synthetically. Polypeptides of less than about 20 amino acid residues may be referred to as "peptides."

A "protein" is a macromolecule comprising one or more polypeptide chains whereby at least one chain has an amino acid length of 100 amino acids or more. A protein may also comprise non-peptidic components, such as carbohydrate groups. Carbohydrates and other non-peptidic substituents may be added to a protein by the cell in which the protein is produced, and may vary with the type of cell. Proteins are defined herein in terms of their amino acid backbone structures; additions such as carbohydrate groups are generally not specified, but may be present nonetheless.

"Heterologous DNA" or "heterologous polypeptide" refers to a DNA molecule or a polypeptide, or a population of DNA molecules or a population of polypeptides, that do not exist naturally within a given host cell. DNA molecules heterologous to a particular host cell may contain DNA derived from the host cell species (i.e. endogenous DNA) so long as that host DNA is combined with non-host DNA (i.e. exogenous DNA). For example, a DNA molecule containing a non-host DNA segment encoding a polypeptide operably linked to a host DNA segment comprising a promoter is considered to be a heterologous DNA molecule. Conversely, a heterologous DNA molecule can comprise an endogenous structural gene operably linked with an exogenous promoter.

A peptide or polypeptide encoded by a non-host DNA molecule is a "heterologous" peptide or polypeptide.

The terms "plasmid" and "vector" as used within this application denote a vehicle for the transfer of genetic material into cells. This material is generally but not exclusively a circular nucleic acid molecule. Depending on the intended purpose of the plasmid it may in addition contain an origin of replication with necessary replication control segments e.g. to allow the replication or transcription of the plasmid in a host.

A "cloning vector" is a nucleic acid molecule, such as a plasmid, cosmid, phageimid or bacterial artificial chromosome (BAC), which has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a resistance gene that is suitable for use in the identification and selection of cells transformed with the cloning vector. Resistance genes typically include genes that provide tetracycline resistance or ampicillin resistance.

An "expression plasmid" is a nucleic acid molecule encoding a protein to be expressed in a host cell. Typically, an expression plasmid comprises a prokaryotic plasmid propagation unit (e.g. for $E.\ coli$, comprising an origin of replication, and a selection marker), a eukaryotic selection marker, and one or more expression cassettes for the expression of the structural gene(s) of interest. An "expression cassette" comprises typically a promoter, a 5' untranslated region, a structural gene, and a 3' untranslated region including a polyadenylation signal. Gene expression is usually placed under the control of a promoter, and such a structural gene is said to be "operably linked to" the promoter. Similarly, a regulatory element and a core promoter are operably linked if the regulatory element modulates the activity of the core promoter.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e. at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers, in mutated from, such as point mutation, or alternatively glycosylated or derivatized forms.

The term "immunoglobulin" refers to a protein consisting of one or more polypeptides substantially encoded by immunoglobulin genes. The recognized immunoglobulin genes include the different constant region genes as well as the myriad immunoglobulin variable region genes. Immunoglobulins may exist in a variety of formats, including, for example, Fv, Fab, and F(ab)$_2$ as well as single chains (scFv) (e.g. Huston, J. S., et al., PNAS USA 85 (1988) 5879-5883; Bird et al., Science 242 (1988) 423-426; and, in general, Hood, L. E., Weissman, I., Wood, W. B., and Wilson, J. H., Immunology, Benjamin/Cummings, Menlo Park, Calif. (1983) and Hunkapiller and Hood, Nature 323 (1986) 15-16).

An immunoglobulin in general comprises at least two light chain polypeptides and two heavy chain polypeptides. Each of the heavy and light polypeptide chains may contain a variable region (generally the amino terminal portion of the polypeptide chain), which contains a binding domain that is able to interact with an antigen. Each of the heavy and light polypeptide chains comprises a constant region (generally the carboxyl terminal portion). The constant region of the heavy chain mediates the binding of the antibody i) to cells bearing an Fc gamma receptor (FcγR), such as phagocytic cells, or ii) to cells bearing the neonatal Fc receptor (FcRn) also known as Brambell receptor. It also mediates the binding to some factors including factors of the classical complement system such as component (Clq).

The variable domain of an immunoglobulin's light or heavy chain in turn comprises different segments, i.e. four framework regions (FR) and three hypervariable regions (CDR).

An "immunoglobulin fragment" denotes a polypeptide comprising one or more segments selected from the group consisting of $C_H1$-domain, hinge-region, $C_H2$-domain, $C_H3$-domain, $C_H4$-domain, $C_L$-domain, $V^H$-domain, $V^L$-domain, framework region 1, framework region 2, framework region 3, framework region 4, hypervariable region 1, hypervariable region 2, and hypervariable region 3, with or without insertions, deletions, and/or mutations.

"A 3' untranslated region comprising a polyadenylation signal" as denoted within this application is a DNA sequence of 50-750 base pairs in length which provides the signal for the cleavage at a specific site at the 3' end of eukaryotic mRNA and the post-transcriptional addition of a sequence of about 100-200 adenine nucleotides (polyA tail) to the cleaved 3' end in the nucleus. Very efficient polyadenylation signals are advisable because inefficient cleavage and polyadenylation can lead to the formation of an operon-like mRNA which can be the reason for an undesired, e.g. plasmid-coded, gene expression.

The terms "host" and "cell" as used within this application denote a cell that is suited for receiving plasmids according to the current invention. Preferably this cell is selected from the group comprising the cells CHO (Chinese Hamster Ovary), BHK (Baby Hamster Kidney) and other rodent cells. Preferred are CHO or derived CHO cells which comprise CHO-K1 cells, CHO-DXB11 cells, CHO-DG44 cells, and CHO cells expressing the EBNA-1 protein. The progeny of the cell provided according to the invention is also included. Also included is the progeny of the cell provided according to the current invention with modifications in consecutive generations that may arise either due to mutation, environmental influences or the degeneracy of the genetic code. The term "cell line" especially denotes a population of cells that can be propagated in vitro for a specified period of time. During this period the cells grow and proliferate by cell division.

The term "transient transfection" as used within this application denotes a process in which the nucleic acid introduced into a cell does not integrate into the genome or chromosomal DNA of that cell. It is in fact maintained as an extrachromosomal element, e.g. as an episome, in the cell. Transcription processes of the nucleic acid of the episome are not affected and e.g. a protein encoded by the nucleic acid of the episome is produced.

The term "stably transformed" as used within this application denotes a heritable and stable integration of exogenous nucleic acid into a host cell genome/chromosome.

The term "biologically active polypeptide" as used herein refers to an organic molecule, e.g. a biological macromolecule such as a peptide, protein, nucleoprotein, mucoprotein, lipoprotein, synthetic polypeptide or protein, that causes a biological effect when administered in artificial biological systems, such as bioassays using cell lines and viruses, or in vivo to an animal, including but not limited to birds and mammals, including humans. This biological effect can be, but is not limited to, enzyme inhibition, activation or allosteric modification, binding to a receptor, either at the binding site or circumferential, blocking or activating a receptor, signal triggering, or antigen binding.

The nucleic acid sequences of the EBV origin of replication oriP, the EBV dyad symmetry element and the EBV family of repeats are denoted in SEQ ID NO: 01 to SEQ ID NO: 03, which have been derived from GenBank-entry V01555. The sequence encoding the EBNA-1 protein is denoted in SEQ ID NO: 04 as nucleic acid sequence and in SEQ ID NO: 05 as amino acid sequence. These sequences have been derived from V01555 (GenBank) and P03211 (SwissProt) respectively.

Different methods are well established and widespread used for protein purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A., Appl. Biochem. Biotech. 75 (1998) 93-102).

The current invention provides a method for the expression of target peptides, polypeptides, and proteins in rodent cells. The current invention further provides a rodent cell for the production of a heterologous peptide, polypeptide, or protein, whereby the structural gene encoding the heterologous peptide, polypeptide or protein is provided by an episome within the rodent cell. Polypeptides or proteins composed of two or more subunits, i.e. for example immunoglobulins, can just as well be produced according to the method of the current invention. For example, in case of an immunoglobulin, which is composed of two pairs of a light and a heavy chain, one episome containing two structural genes encoding both chains of the immunoglobulin can be used. Alternatively two episomes, e.g. one containing the structural gene encoding the light chain and one containing the structural gene encoding the heavy chain, may be used.

A promoter directed to the expression of the EBNA-1-protein is used in the current invention. Preferably a strong promoter is used, preferably a heterologous strong promoter, such as e.g. CMV, is used. The stable integration of an expression cassette for the EBNA-1-protein into the chromosomal DNA resulted in a modified rodent cell expressing the EBNA-1-protein, i.e. the structural gene encoding the EBNA-1 protein and the promoter are integrated operably linked into the chromosomal DNA.

To illustrate the subject matter of the current invention, the invention will be described in the following. As first step a basic rodent cell line is constructed, which expresses the EBNA-1-protein. Preferably a basic rodent cell line is constructed, which in culture steadily expresses the EBNA-1-protein. Thereafter a plasmid, containing an expression cassette for one or more heterologous polypeptides, is designed and introduced into the basic rodent cell line. The obtained cell line, expressing the EBNA-1-protein and carrying plasmid(s) for the expression of heterologous polypeptide(s), is cultivated under conditions suitable for the expression of the heterologous polypeptide(s) (see examples 1 to 4).

The following description and examples are given with the purpose of illustration of the invention and not on the purpose of limiting the scope of the invention.

Construction of the Host Cell Line

The host cell of the current invention provides a nucleic acid encoding the EBNA-1 protein.

The construction of a plasmid containing an expression cassette with the structural gene encoding the EBNA-1-protein is described in example 2a). An annotated map of the plasmid is shown in FIG. 1.

Rodent cells were transfected with this plasmid. After selection of transfected cells under selective cultivation conditions with G418 as selective agent, transformants were picked, expanded and tested for EBNA-1 protein production.

The constructed plasmid for the formation of the basic rodent cell line shall not contain a functional copy of the EBV oriP sequence. This includes both elements of the oriP, the dyad symmetry element and the family of repeats.

Construction of Expression Plasmids

For the expression of a heterologous peptide, polypeptide, or protein expression plasmids containing expression cassettes for the corresponding structural genes have to be constructed.

As an example protein the monoclonal human anti-IGF-1R antibody (cf. US 2005/0008642) was chosen. For the production of the HuMab anti-IGF-1R, using the basic rodent cell line of the invention, expression plasmids have been constructed (see example 3 and FIGS. 3 to 5). The constructed plasmids for the expression of the heterologous polypeptide shall not contain a functional copy of the EBNA-1 structural gene.

Generally speaking, the structural genes encoding the HuMab anti-IGF-1R light chain variable region ($V^L$) and the human κ-light chain constant region ($C_L$) were joined as were the structural genes for the HuMab anti-IGF-1R heavy chain variable region ($V^H$) and the human γ1-heavy chain constant region ($C_H1$-hinge-$C_H2$-$C_H3$) by subcloning and overlapping PCR. These constructs have been subsequently inserted into mammalian cell expression vectors either lacking or carrying the EBV oriP.

Expression of the Polypeptides in the Basic Rodent Cell Line

The basic rodent cell line according to the invention was transfected with one or more of the constructed expression plasmids. The culturing of the transfected cells was done under conditions suitable for the expression of the heterologous polypeptide(s), e.g. under transient transfection.

Generally speaking, culturing under transient transfection permits that the transfected expression plasmid(s) is (are) not integrated into the chromosome of the host cell due to the absence of a selective pressure exerted by a selection agent. Owing to these not selective growth conditions the expression plasmids are not replicated in all cells of the culture at 100% frequency. This causes a slow decline in the overall protein expression rate. The cultivation is generally carried out until the concentration of the expressed protein in the culture reaches a maximum value. Preferably the cultivation is performed for up to twenty days, preferably for up to ten days, more preferably for five to ten days.

After this period of time the supernatant was separated and the produced secreted immunoglobulin was isolated and purified according to standard techniques known to a person skilled in the art.

Beside the batch cultivation as described above, a split-batch process can be used for the cultivation of the cells. During the split-batch cultivation process the nutrient medium is exchanged after half of the cultivation period.

Thus an objective of the current invention was to provide a method for the expression of a heterologous polypeptide that permits to produce in a short time said heterologous polypeptide with a glycosylation pattern similar to that of mammalian cells, preferably human cells. It has now surprisingly been found that a method according to the current invention fulfills this need.

The cell line on which this method is based is a rodent cell, preferably a CHO cell, that is in compliance with the regulations set up for cells lines for the production of therapeutic polypeptides and proteins, i.e. that does not contain pro-oncogenes such as large T-antigen of Polyoma virus.

It has been surprisingly found that in a cell stably transfected with a structural gene encoding the EBNA-1 protein, preferably operably linked to a promoter, extrachromosomal elements, e.g. expression plasmids, possessing an Epstein-Barr-Virus (EBV) origin of replication and without, i.e. not containing, a structural gene encoding the EBNA-1 protein are functionable in the expression of heterologous polypeptides. Generally in a method according to the invention two elements derived from the Epstein-Barr-Virus are use the origin of replication (oriP) and the structural gene encoding the EBNA-1 protein.

One aspect of the current invention is a method for the expression of a heterologous polypeptide in a rodent cell, characterized in that said method comprises
 a) providing a rodent cell stably transfected with the structural gene encoding the EBNA-1 protein,
 b) transfecting said rodent cell with an expression plasmid comprising an Epstein-Barr-Virus (EBV) origin of replication (oriP),
 c) culturing said transfected cell under conditions suitable for the expression of said heterologous polypeptide,
 d) recovering said heterologous polypeptide from the culture.

In one embodiment said heterologous polypeptide is an immunoglobulin or an immunoglobulin fragment, preferably said immunoglobulin is an immunoglobulin G or an immunoglobulin E.

In one embodiment said heterologous polypeptide is a secreted heterologous polypeptide and said heterologous polypeptide is recovered from the culture medium.

In one embodiment said rodent cell is a CHO cell.

In one embodiment said structural gene encoding the EBNA-1 protein is operably linked to a promoter, preferably a strong promoter, especially preferred to the promoter derived from CMV.

In one embodiment said expression plasmid comprises as single EBV-derived element an Epstein-Barr-Virus (EBV) origin of replication (oriP).

In one embodiment said expression plasmid comprises no structural gene encoding the EBNA-1 protein.

In one embodiment said expression plasmid in addition comprises
 a prokaryotic origin of replication
 a selection marker
 an expression cassette suitable for the expression of a heterologous polypeptide in said rodent cell, whereby said expression cassette comprises a promoter sequence, a 5' untranslated region, a nucleic acid sequence (structural gene) encoding said heterologous protein, and a 3' untranslated region comprising a polyadenylation signal.

In one embodiment if the heterologous polypeptide is a secreted heterologous polypeptide said expression cassette in addition comprises a signal sequence operably linked with the structural gene encoding said heterologous polypeptide.

In one embodiment the method for the expression of a heterologous polypeptide is performed as batch process, as split-batch process, or as continuous process. In a preferred embodiment said method is performed as batch or split-batch process.

In one embodiment the method for the expression of a heterologous polypeptide in addition contains a step e) purifying said heterologous polypeptide.

General chromatographic methods and their use are known to a person skilled in the art. See for example, Chromatography, 5$^{th}$ edition, Part A: Fundamentals and Techniques, Heftmann, E. (ed.), Elsevier Science Publishing Company, New York (1992); Advanced Chromatographic and Electromigration Methods in Biosciences, Deyl, Z. (ed.), Elsevier Science BV, Amsterdam, The Netherlands (1998); Chromatography Today, Poole, C. F., and Poole, S. K., Elsevier Science Publishing Company, New York (1991), Scopes, Protein Purification: Principles and Practice (1982); Sambrook, J., et al. (ed.), Molecular Cloning: A Laboratory Manual, Second Edition, Cold Spring Harbor Laboratory Press, Cold Spring Harbor, N.Y. (1989), or Current Protocols in Molecular Biology, Ausubel, F. M., et al. (eds)., John Wiley & Sons, Inc., New York.

The purification process of immunoglobulins in general comprises a multistep chromatographic part. In the first step non-immunoglobulin polypeptides and proteins are separated from the immunoglobulin fraction by an affinity chromatography, e.g. with protein A. Afterwards an ion exchange chromatography can be performed to disunite the individual immunoglobulin classes and to remove traces of protein A, which has been coeluted from the first column. Finally a third chromatographic step is necessary to separate immunoglobulin monomers from multimers and fragments of the same class. Sometimes the amount of aggregates is high (5% or more) and it is not possible to separate them efficiently in the third purification step necessitating further purification steps.

With the recombinant production of specific immunoglobulins the separation step for the separation of different immunoglobulin classes is dispensable. Thus the overall purification process of recombinantly produced immunoglobulins may be reduced to two chromatographic steps.

The protein A eluate is in general chromatographically processed on a cation exchange material at pH values below the isoelectric point of the respective immunoglobulin protein.

In one embodiment the method for the expression of a heterologous polypeptide is performed under transient transfection.

In one embodiment of said method for the expression of a heterologous polypeptide said structural gene encoding the EBNA-1 protein is a full length structural gene (SEQ ID NO: 4) encoding the EBNA-1 protein and said expression plasmid comprises no full length structural gene (SEQ ID NO: 4) encoding the EBNA-1 protein.

The following examples, sequence listing and figures are provided to aid the understanding of the present invention, the true scope of which is set forth in the appended claims. It is understood that modifications can be made in the procedures set forth without departing from the spirit of the invention.

Figure 2:
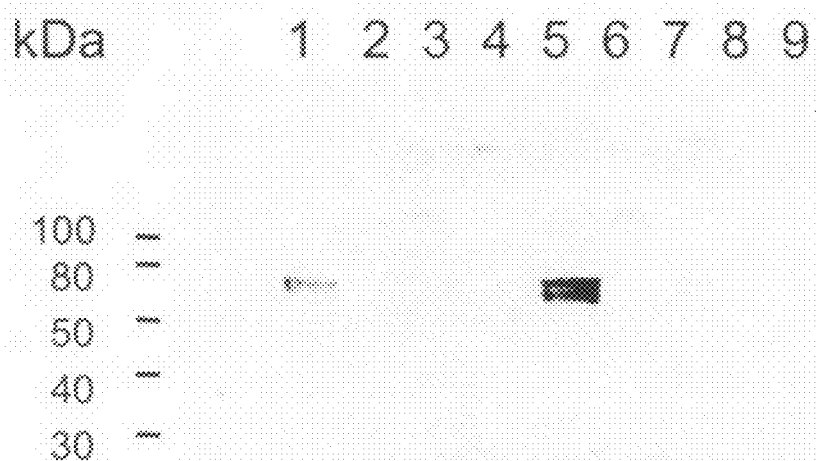
Figure 2:
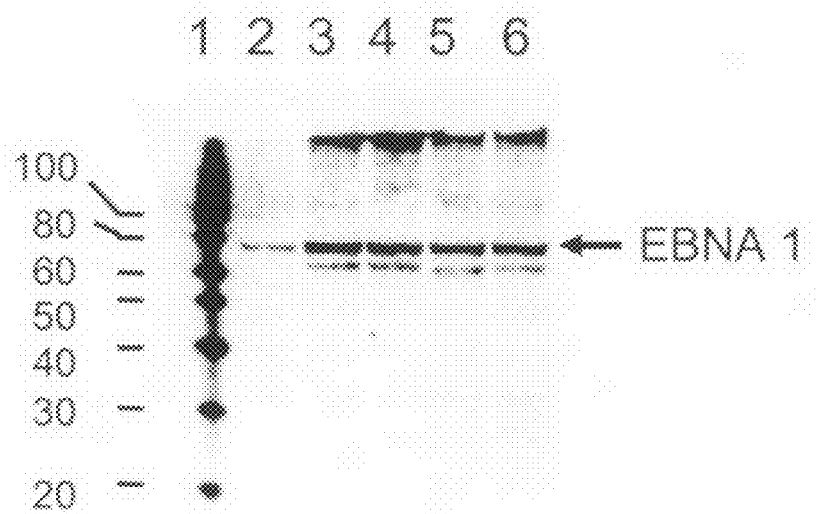

Legend to FIG. 2a): lane 1: Protein Standard; lane 2: 293 EBNA, 100 μg protein; lane 3: DG-700-IIIE3sub1, 4th passage, day 6, 100 μg protein; lane 4: DG-700-IIIE3sub1, 15th passage, day 37, 100 μg protein; lane 5: DG-700-IIIE3sub1, 18th passage, day 48, 100 μg protein; lane 6: DG-700-IIIE3sub1, 20th passage, day 54, 100 μg protein.

Figure 3:
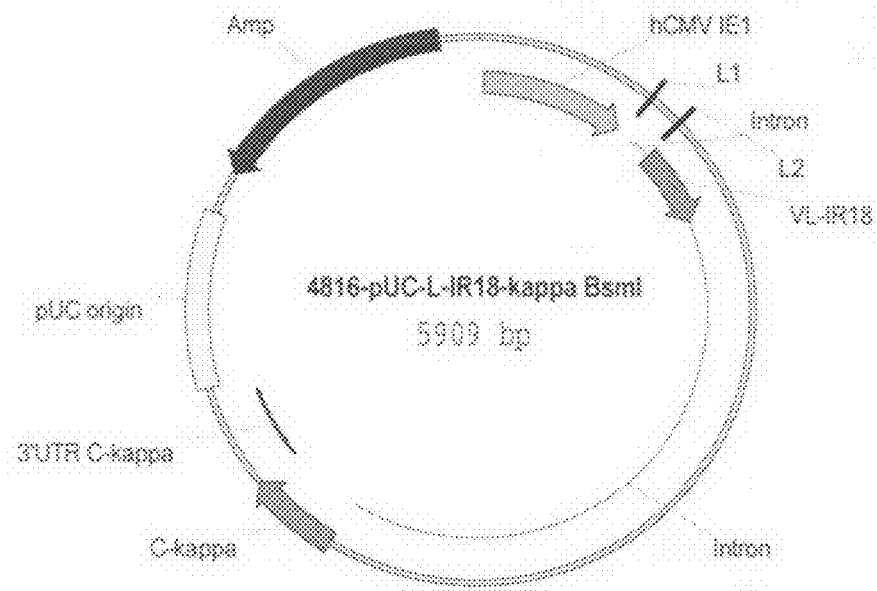
Figure 3:
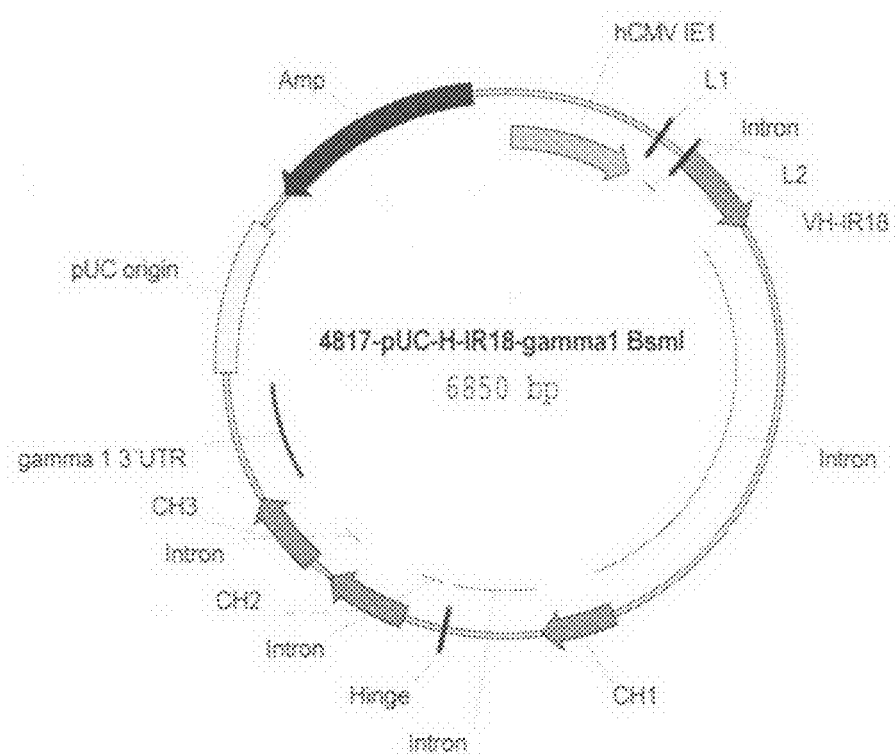
Figure 4:
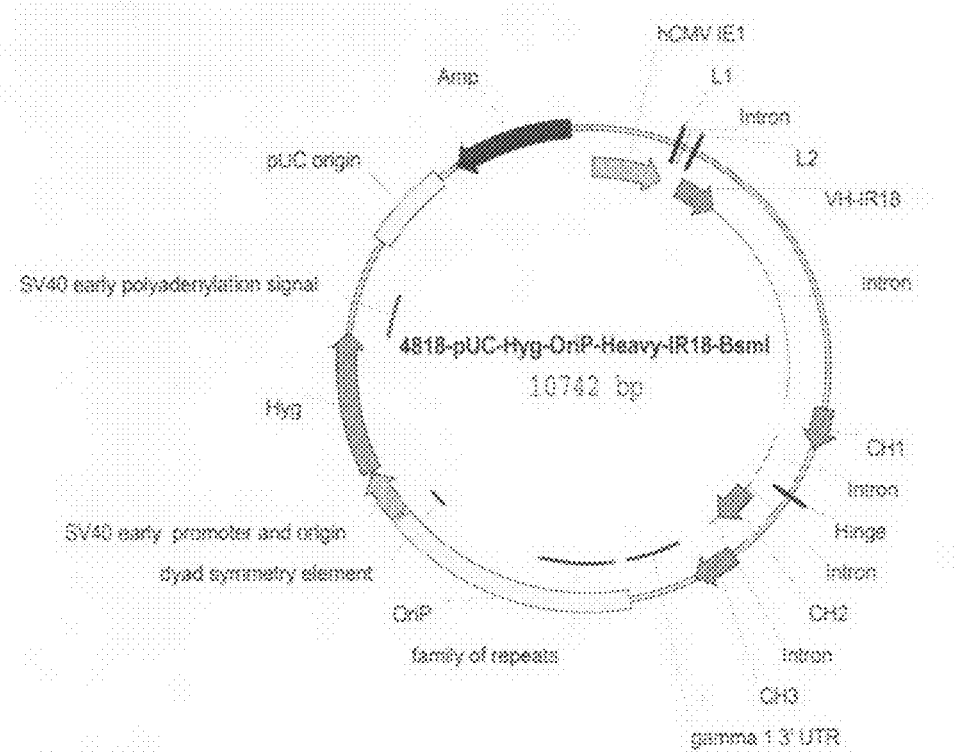
Figure 4:
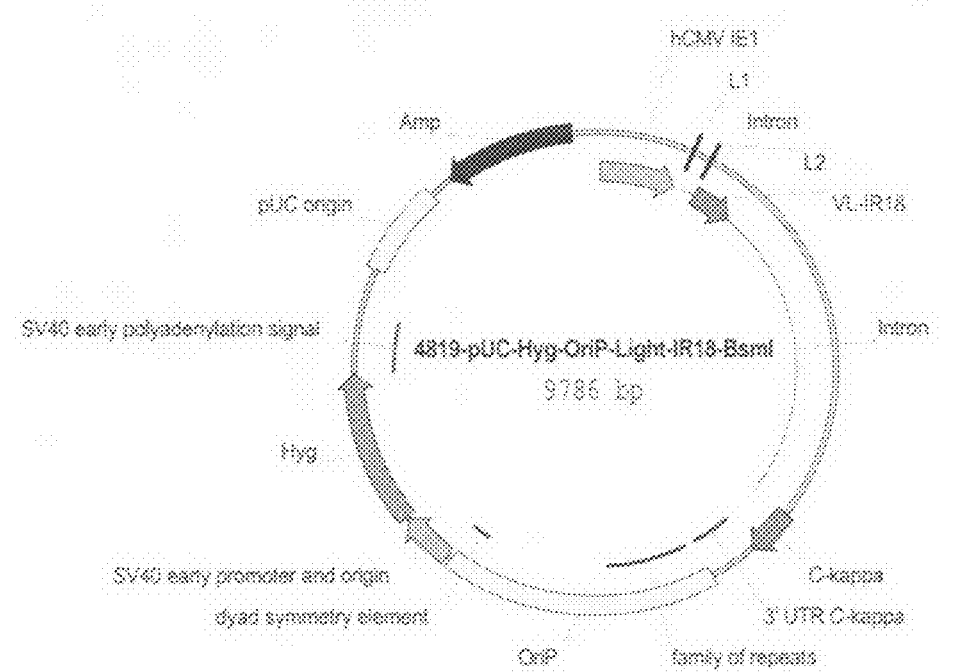
Figure 5:
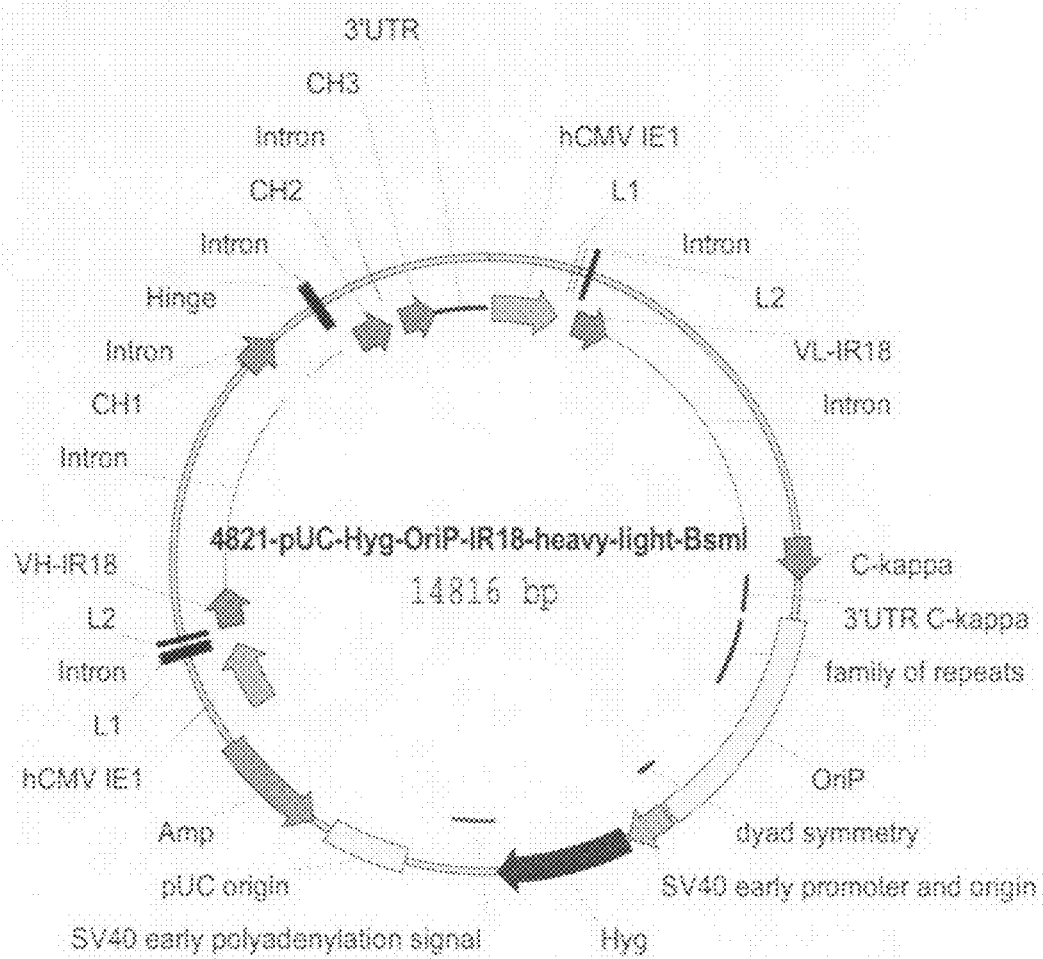
Figure 6:
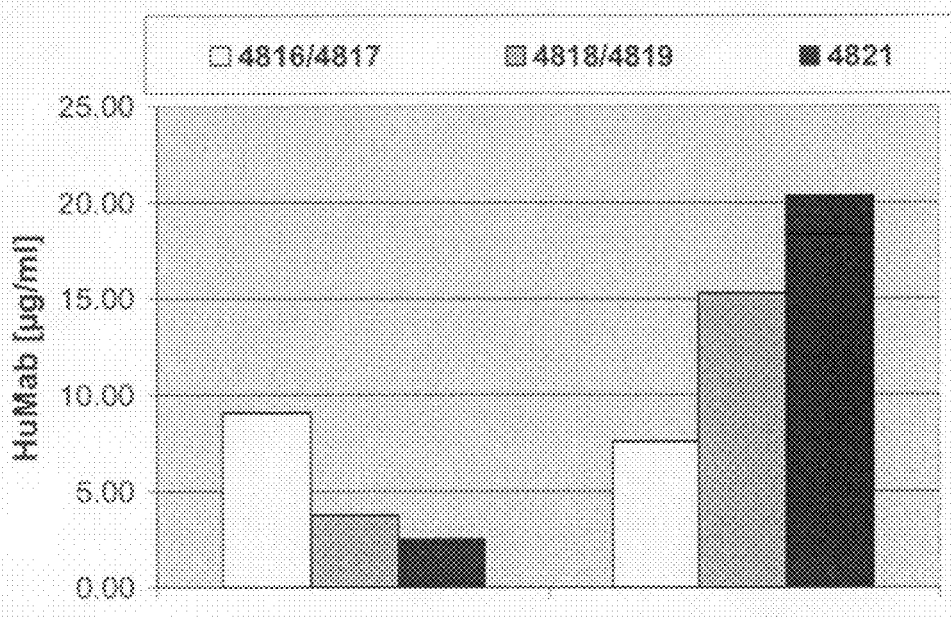
Figure 6:
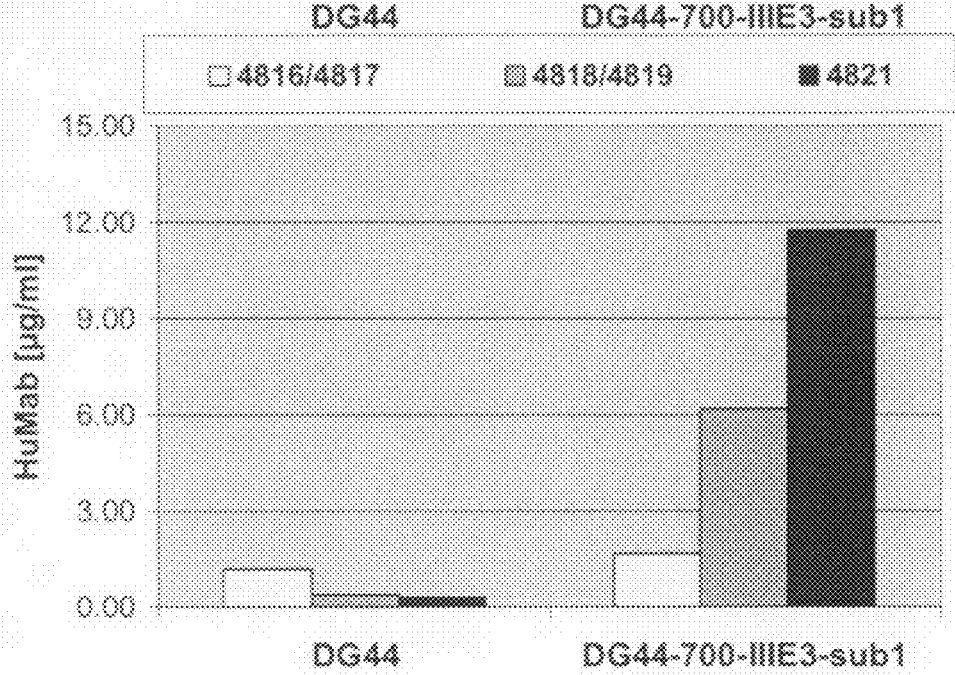

FIG. 3a Map of plasmid p4816-pUC-L-IR18-kappa BsmI
FIG. 3b Map of plasmid p4817-pUC-H-IR18-gamma1 BsmI
FIG. 4a Map of plasmid p4818-pUC-Hyg-OriP-Heavy-IR18-BsmI
FIG. 4b Map of plasmid p4819-pUC-Hyg-OriP-Light-IR18-BsmI
FIG. 5 Map of plasmid p4821-pUC-Hyg-OriP-IR18-heavy-light-BsmI
FIG. 6 Comparison of the expression of antibody in different cell lines and by different expression plasmids

DESCRIPTION OF THE SEQUENCES

SEQ ID NO: 01 Nucleic acid sequence of the EBV oriP; V01555 (GenBank); Yates, J. L., et al., Proc Natl Acad Sci USA 81 (1984) 3806-3806.

SEQ ID NO: 02 Nucleic acid sequence of the EBV dyad symmetry element; V01555 (GenBank); Reisman, D., et al., Mol. Cell. Biol. 5 (1985) 1822-1832.

SEQ ID NO: 03 Nucleic acid sequence of the EBV family of repeats; V01555 (GenBank); Reisman et al., 1985.

SEQ ID NO: 04 Nucleic acid sequence encoding the EBNA-1-protein; V01555 (GenBank).

SEQ ID NO: 05 Amino acid sequence of the EBNA-1-protein; P03211 (SwissProt).

SEQ ID NO: 06 Primer oligonucleotide 1.
SEQ ID NO: 07 Primer oligonucleotide 2.
SEQ ID NO: 08 Primer oligonucleotide 3.
SEQ ID NO: 09 Primer oligonucleotide 4

DESCRIPTION OF THE EXAMPLES

Example 1 General techniques.
Example 2 Construction of CHO cell lines expressing the EBNA-1 protein.
Example 3 Construction of plasmids carrying the EBV oriP and expression cassettes for the light and heavy chains of human monoclonal anti-IGF-1R antibody.
Example 4 Production of antibodies by EBNA-1-positive DG-700-IIIE3sub1 cells from oriP carrying plasmids.

Example 1

General Techniques a) Recombinant DNA Techniques

Standard methods were used to manipulate DNA as described in Sambrook, J., Fritsch, E. F. and Maniatis, T. (1989), Molecular cloning: A laboratory manual. Cold Spring Harbor Laboratory Press, Cold Spring Harbor, N.Y. The molecular biological reagents were used according to the manufacturer's instructions.

b) DNA Sequence Determination

DNA sequences were determined by double strand sequencing performed at MediGenomix GmbH (Martinsried, Germany).

c) DNA and Protein Sequence Analysis and Sequence Data Management

The GCG's (Genetics Computer Group, Madison, Wis.) software package version 10.2 and Infomax's Vector NTI Advance suite version 8.0 was used for sequence creation, mapping, analysis, annotation and illustration.

d) Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

e) Western Blot Analysis of EBNA-1 Expression

Cells were harvested by centrifugation at 200×g, washed with PBS (phosphate buffered saline), and incubated in lysis buffer (50 mM Tris*HCl (tris (hydroxymethyl) amino methane hydrochloride), pH 8.0, 120 mM NaCl, 0.5% (v/v) Nonidet® P40, 10% (v/v) glycerol, 5 mM DTT (Dithiothreitol), 1 mM EGTA (ethylene-bis(oxyethylenenitrilo) tetraacetic acid), 1% (v/v) Trasylol®, 2 mM PMSF (phenylmethanesulfonyl fluoride), 50 µg/ml Leupeptin) for 30 minutes on ice. After centrifugation at 13,000×g the soluble supernatant was harvested and tested for protein concentration using Bio-Rad Protein assay (Cat-Nr.: 5000-0001) according to the manufactures protocol.

SDS/polyacrylamide gel electrophoresis (sodium dodecyl sulfate, SDS-PAGE) and electro-blotting of proteins were performed using the NuPAGE® gel system (Invitrogen) according to the manufacturer's recommendations. In brief, protein lysate (100 µg protein) was combined with the 4 fold volume of reducing LDS (lithium dodecyl sulfate) sample buffer, incubated at 70° C. for 10 minutes and loaded onto 10% NuPAGE® Novex Bis/Tris gels (Invitrogen, Cat-Nr.: NP0301). Separation of proteins took place in reducing NuPAGE® MES SDS (4-morpholinoethanesulfonic acid/sodium dodecyl sulfate) running buffer. For electro-transfer of proteins from SDS/polyacrylamide gels standard nylon membranes were used. After electro-transfer membranes were washed in 50 mM Tris*HCl, pH 7.5, 150 mM NaCl (TBS, tris buffered saline) and nonspecific binding sites were blocked over night at 4° C. in TBS, 1% (w/v) Western Blocking Reagent (Roche, Cat Nr.: 11921673001). Mouse monoclonal antibody E8.26 (Oncogene, Cat Nr.: DP15L) directed against EBNA-1 was used as primary antibody at a dilution of 1:1,000 in TBS, 1% (w/v) Western Blocking Solution. After two washes in TBS and two washes in TBS supplemented with 0.05% (v/v) Tween-20 (TBST), a peroxidase-coupled anti-mouse/anti-rabbit IgG antibody (Roche, Cat. No. 1520709) was used as secondary antibody at a dilution of 1:10,000 in TBS with 1% (w/v) Western Blocking Solution. After two washes with TBST and three washes with TBS, bound peroxidase conjugates were detected by chemoluminescence using LumiLightPlus substrate solution (Roche, Cat. Nr. 12015196001) and Lumi-Imager F1 analyzer (Roche Molecular Biochemicals).

f) Quantification of Recombinant Antibodies in Cell Culture Supernatants

Antibodies in cell culture supernatants were quantified by a competitive immunoassay using the Human Fc Detection Kit (Cis Bio, Cat-Nr.: 62HFCPEB). The assay is based on the HTRF® technology (Homogeneous Time-Resolved Fluorescence). In brief, samples were diluted 1:10 to 1:100 in Diluent Buffer. 50 µl of diluted sample were combined with 25 µl anti-human-IgG Fc-cryptate and 25 µl human IgG-XL665 in 96-well OptiPlates (Perkin Elmer, Cat-Nr.: 6005279). Assay mixtures were incubated over night at room temperature. After excitation at 320 nm, fluorescence emission was measured at 620 nm and 665 nm using a Victor 1420 analyzer (Perkin-Elmer). Antibody concentrations were deduced from the 665 nm/620 nm ratio by comparison with a calibration curve.

Example 2

Figure 1:
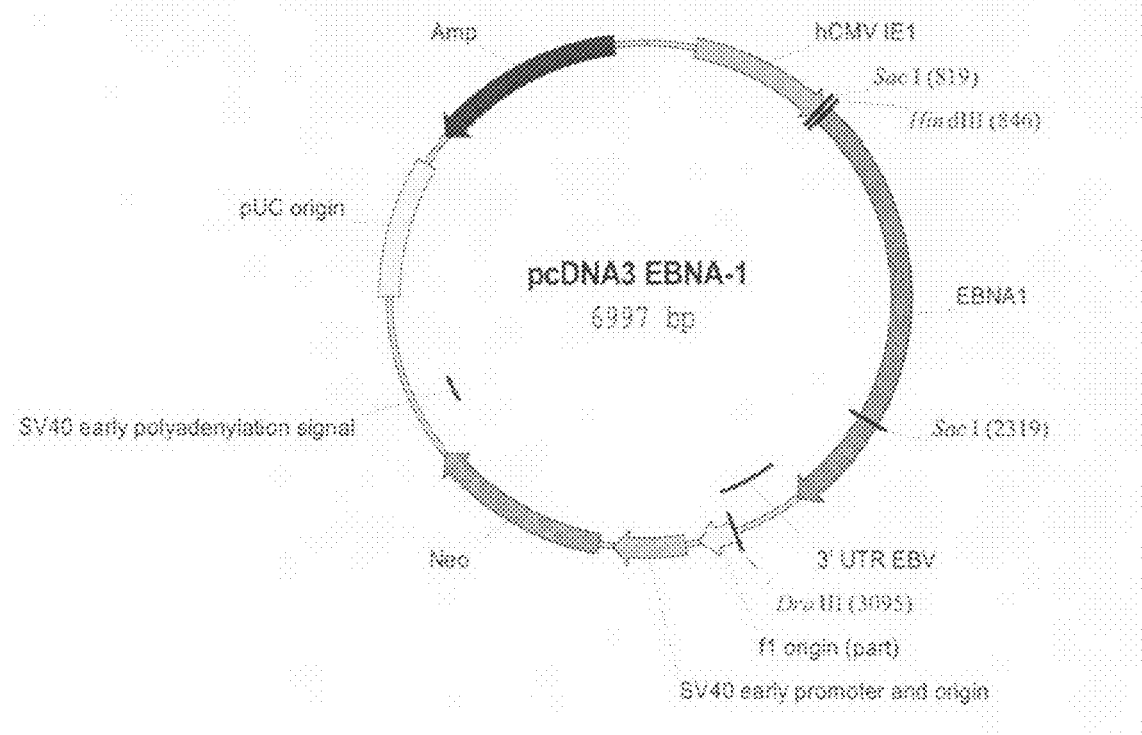
FIG. 1 Map of plasmid pcDNA3_EBNA-1; plasmid containing the expression cassette for the EBNA-1-protein FIG. 2 Western-Blot analyses of the EBNA-1 expression.
Legend to FIG. 2a): lane 1: 293 EBNA, 65 μg protein; lane 2: CHO-DG44, 100 μg protein; lane 3: DG-700-IIIH7, 100 μg protein; lane 4: DG-700-IIID9, 100 μg protein; lane 5: DG-700-IIIE3, 100 μg protein; lane 6: DG-700-IIIE8, 100 μg protein; lane 7: DG-700-IIIF1, 100 μg protein; lane 8: DG-700-IIIG10, 100 μg protein; lane 9: DG-700-IIIH8, 100 μg protein.

Construction of CHO Cell Lines Expressing the EBNA-1 Protein a) Construction of Plasmid pcDNA3_EBNA-1 for Expression of the EBNA-1-Protein in CHO Cells Plasmid pcDNA3.1 (Invitrogen, Cat-Nr.: V790-20) was cut with the restriction nucleases SacI and DraIII and the resulting 4715 bp fragment was ligated to a DNA linker obtained by annealing oligonucleotide 1 (SEQ ID NO: 06) and oligonucleotide 2 (SEQ ID NO: 07). The resulting plasmid was cut with HindIII and DraIII. The 4748 bp vector fragment was ligated to an EBNA-1 encoding HindIII/DraIII cDNA fragment obtained by polymerase chain reaction using pCEP4 (Invitrogen, Cat-Nr.: V044-50) as a template and oligonucleotides 3 (SEQ ID NO: 08) and oligonucleotide 4 (SEQ ID NO: 09) as primers. The eukaryotic expression plasmid for EBNA-1 was named pcDNA3_EBNA-1 (FIG. 1).

b) Transfection of CHO Cells with pcDNA3_EBNA-1 and Selection of Stable Transfectants CHO-DG44 cells pre-adapted to serum free suspension culture were maintained in spinner flasks in DHI medium (Schlaeger, E. J., J. Immunol. Methods 194 (1996) 191-199) in a humidified incubator at 37° C. with 5% pCO$_2$.

Prior to transfection cells were seeded into 24-well plates at 1×10$^6$ cells/ml. Transfection was performed using LipofectAmine 2000 (Invitrogen, Cat-Nr.: 11668-027) according to the manufacturers protocol. In brief, DNA and LipofectAmine 2000 were diluted in OptiMEM I-medium (Invitrogen, Cat-Nr.: 31985-047) and combined in a ratio of µg DNA to µl LipofectAmine 2000 of 1:3 to 1:6. After 20 minutes incubation at room temperature the mixture was added to the cells. After 24 hours the cells were diluted in DHI medium and seeded in 96 well-plates at 300 cells/well. After an additional 24 hours G418 was added to the medium at 700 µg/ml. Ten days after transfection G418 resistant colonies were expanded and analyzed for expression of the EBNA-1-protein by Western Blot hybridization (FIG. 2a)). HEK 293 cells steadily expressing the EBNA-1-protein (HEK 293 EBNA or HEK 293 E) and untransfected CHO-DG44 cells have been used as references. Clone DG-700-IIIE3 was strongly positive for EBNA-1 and was subcloned by limiting dilution. The EBNA-1-positive subclone DG-700-IIIE3sub1 was continuously cultivated and checked for EBNA-1 expression by Western Blot hybridization (FIG. 2b)). As shown in FIG. 2b the EBNA-1 protein level remained unchanged during 54 days of cultivation.

Example 3

Construction of Plasmids Carrying the EBV oriP and Expression Cassettes for the Light and Heavy Chains of Human Monoclonal Anti-IGF-1R Antibody The gene segments encoding the anti-IGF-1R antibody light chain variable ($V^L$) region and human κ-light chain constant ($C_L$) region were precisely joined as were genes for the anti-IGF-1R antibody variable heavy chain ($V^H$) region and human γ1-heavy chain constant ($C_H1$-$C_H2$-$C_H3$) region by subcloning and overlapping PCR. The DNA sequences encoding the anti-IGF-1R antibody structural genes (κ-light and γ1-heavy chain) were confirmed by DNA sequencing and subsequently inserted into mammalian cell expression vectors either lacking or carrying the EBV oriP.

The HuMab anti-IR18 κ-light chain expression vector p4816-pUC-L-IR-18-kappa-BsmI (p4816) is composed of the following elements:

origin of replication from the vector pUC18 which allows replication of this plasmid in *E. coli* (pUC ori)

a β-lactamase gene which confers ampicillin resistance in *E. coli* (Amp)

a transcription unit for the expression of the anti-IGF-1R antibody κ-light chain composed of the following elements:

the major immediate-early promoter and enhancer from the human cytomegalovirus (hCMV IE1)

a synthetic 5'-UTR including a Kozak sequence a murine immunoglobulin heavy chain signal sequence including the signal sequence intron (L1_Intron_L2)

the cloned anti-IGF-1R antibody variable light chain cDNA arranged with a unique BsmI restriction site at the 5' end and a splice donor site and a unique NotI restriction site at the 3' end ($V^L$)

the genomic human kappa-light gene constant region, including the intronic mouse Ig-kappa enhancer [NotI_mouse-Ig-kappa-enhancer-intron-2_human-intron-2_C-kappa]

the human kappa-immunoglobulin 3' UTR including the polyadenylation signal sequence (3' UTR C-kappa)

the unique restriction sites Sse8371I and FseI at the 5' and 3' end, respectively, to enable the transfer of the expression cassette into alternative expression plasmids.

The plasmid map of p4816-pUC-L-IR-18-kappa-BsmI is shown in FIG. 3a).

The anti-IGF-1R antibody gamma1-heavy chain expression vector p4817-pUC-H-IR-18-gamma1-BsmI (p4817) is composed of the following elements:

an origin of replication from the vector pUC18 which allows replication of this plasmid in *E. coli* (pUC ori)

a beta-lactamase gene which confers ampicillin resistance in *E. coli* (Amp)

a transcription unit for the expression of the anti-IGF-1R antibody gamma1-heavy chain composed of the following elements:

the major immediate-early promoter and enhancer from the human cytomegalovirus (hCMV IE1)

a synthetic 5'-UTR, including a Kozak sequence a murine immunoglobulin heavy chain signal sequence including the signal sequence intron (L1_Intron_L2)

the cloned anti-IGF-1R antibody variable heavy chain cDNA arranged with a unique BsmI restriction site at the 5' and a splice donor site and a unique NotI restriction site at the 3' end the genomic human γ1-heavy gene constant region, including the mouse Ig mu(μ)-enhancer [NotI_mouse-Ig-μ-enhancer-human-intron-2_$C_H1$-$C_H2$-$C_H3$ with intervening introns]

the human γ1-immunoglobulin 3' UTR including the polyadenylation signal sequence the unique restriction sites SgrAI and AscI at the 5' and 3' end, respectively, to enable the transfer of the expression cassette into alternative expression plasmids.

The plasmid map of p4817-pUC-L-IR-18-gamma1-BsmI is shown in FIG. 3b).

The plasmids p4818-pUC-Hyg-OriP-Heavy-IR18-BsmI (p4818) and p4819-pUC-Hyg-OriP-Light-IR18-BsmI (p4819), which are shown in FIG. 4, were derived from the plasmids p4817-pUC-H-IR18-gamma1-BsmI and p4816-pUC-L-IR18-kappa-BsmI, respectively, by introduction of two elements:

a hygromycin resistance gene suitable as a selectable marker in eukaryotic cells the origin of replication, oriP, of Epstein-Barr virus The plasmid maps of p4818-pUC-Hyg-OriP-Heavy-IR18-BsmI and p4819-pUC-Hyg-OriP-Light-IR18-BsmI are shown in FIG. 4a) and FIG. 4b).

Plasmid p4821-pUC-Hyg-OriP-IR18-heavy-light-BsmI was constructed by introducing the SgrAI/AscI-fragment of p4818 comprising the gamma1-heavy chain transcription unit into the SgrAI and AscI restriction sites of p4819. The resulting plasmid contains the same elements as p4819, including the EBV oriP and the transcription unit for the kappa-light chain, plus the gamma1-heavy chain transcription unit.

The plasmid map of p4821-pUC-Hyg-OriP-IR18-heavy-light-BsmI is shown in FIG. 5.

Example 4

Production of Antibodies by EBNA-1-Positive Dg-700-IIIE3Sub1 Cells from oriP Carrying Plasmids DG-700-IIIE3sub1 and unmodified CHO-DG44 type cells were maintained in ProCHO4-CDM (Cambrex, Cat-Nr.: BE12-029Q), 2 mM Glutamine, 2% (v/v) 50×HT supplement (Invitrogen, Cat-Nr.: 41065-012) and 300 μg/ml G418 in stationary culture at 37° C. with 5% $CO_2$. One hour prior to transfection cells were harvested by centrifugation and resuspended in DHI medium (Schlaeger, E. J., J. Immunol. Methods 194 (1996) 191-199) at $0.5 \times 10^6$ cells/ml.

Transfection was performed using LipofectAmine 2000 (Invitrogen, Cat-Nr.: 11668-027). For transfection of 1 ml culture volume the following components were combined: 200 μl OptiMEM I (Invitrogen, Cat-Nr.: 31985-047), 2 μg DNA and 6 μl LipofectAmine. After 5 to 30 minutes incubation at room temperature the mixture was added to the cells. Five to ten days after transfection the cell culture supernatant was collected and tested for antibody concentration as described in example 1f).

Three different sets of plasmids have been transfected into CHO-DG44 cell line or the EBNA-1-expressing CHO-DG44 derived cell line DG-700-IIIE3sub1. Plasmid p4816 for the expression of antibody light chain was co-transfected with p4817 for expression of antibody heavy chain. Both plasmids lack the EBV oriP. Plasmid p4819 for expression of antibody light chain was co-transfected with p4818 for expression of antibody heavy chain. Both plasmids carry the EBV oriP. Finally, plasmid p4821 for expression of both antibody light and heavy chain was transfected alone. Plasmid p4821 carries the EBV oriP.

As shown in FIG. 6, transfection of oriP carrying plasmids p4818 and p4819 in EBNA-1-positive DG-700-IIIE3sub1 cells resulted in a two- to threefold increased expression of antibody as compared to transfection of p4816 and p4817 without oriP into the same cell line or into EBNA-1-negative CHO-DG44 cells. Expression of the antibody in DG-700-IIIE3sub1 cells was even stronger when the expression cassettes for antibody light and heavy chain were combined in a single oriP carrying plasmid like p4821. In contrast, oriP carrying plasmids p4817/p4818 and p4821 did not yield increased antibody expression levels in EBNA-1-negative CHO-DG44 cells. As a result, maximum expression of the immunoglobulin was achieved, when oriP carrying plasmids were transfected into EBNA-1-positive CHO cells.

The invention claimed is:

1. A Chinese Hamster Ovary (CHO) cell, wherein said CHO cell
   a) contains a structural gene located in the genome of said CHO cell which encodes and expresses the Epstein Barr Virus Nuclear Antigen 1 (EBNA-1);
   b) contains an episome, wherein said episome comprises
      (i) a prokaryotic origin of replication;
      (ii) a selection marker;
      (iii) a single Epstein Barr Virus (EBV) derived element, wherein the single EBV derived element is an EBV origin of replication (oriP);
      (iv) an expression cassette suitable for the expression of a heterologous polypeptide in said CHO cell, whereby said expression cassette comprises a promoter sequence, a 5' untranslated region, a nucleic acid sequence encoding said heterologous polypeptide and a 3' untranslated region comprising a polyadenylation signal;
      wherein said episome does not contain a nucleic acid encoding EBNA-1; and
   c) does not contain the large T-antigen of Polyoma virus.

2. The CHO cell of claim 1, wherein the structural gene encoding the EBNA-1 protein is operably linked to a heterologous promoter.

3. A kit for the production of a CHO cell of claim 1, wherein said kit comprises
   a) a CHO cell which does not contain the large T-antigen of Polyoma virus;
   b) a first plasmid comprising
      (i) a prokaryotic origin of replication;
      (ii) a selection marker;
      (iii) a functional expression cassette for the Epstein Barr Virus Nuclear Antigen 1 (EBNA-1), whereby said expression cassette comprises a promoter sequence, a 5' untranslated region, a nucleic acid sequence encoding EBNA-1 and a 3' untranslated region comprising a polyadenylation signal;
   c) a second plasmid comprising
      (i) a prokaryotic origin of replication;
      (ii) a selection marker;
      (iii) an Epstein-Barr-Virus (EBV) origin of replication (oriP) as single EBV derived element;
      (iv) an expression cassette suitable for the expression of a heterologous polypeptide in said rodent cell, whereby said expression cassette comprises a promoter sequence, a 5' untranslated region, a cloning site for the introduction of a nucleic acid sequence and a 3' untranslated region comprising a polyadenylation signal,
      (v) no structural gene encoding the ENBA-1 protein.

4. A method for obtaining the CHO cell of claim 1, wherein said method comprises the steps of
   a) introducing a first plasmid into a CHO cell, wherein the first plasmid comprises:
      (i) a prokaryotic origin of replication;
      (ii) a selection marker;
      (iii) a functional expression cassette for the Epstein Barr Virus Nuclear Antigen 1 (EBNA-1), whereby said expression cassette comprises a promoter sequence, a 5' untranslated region, a nucleic acid sequence encoding EBNA-1 and a 3' untranslated sequence comprising a polyadenylation signal;
      and wherein the CHO cell does not contain the large T-antigen of Polyoma virus;
   b) selecting a stably transformed CHO cell from step a);
   c) introducing at least one to four further plasmids into the stably transformed CHO cell, wherein the at least one to four further plasmids comprise
      (i) a prokaryotic origin of replication;
      (ii) a selection marker;
      (iii) an Epstein-Barr-Virus (EBV) origin of replication (oriP) as single EBV derived element;
      (iv) an expression cassette suitable for the expression of a heterologous polypeptide in said transformed CHO cell, whereby said expression cassette comprises a promoter sequence, a 5' untranslated region, a nucleic acid sequence encoding a heterologous polypeptide and a 3' untranslated region with a polyadenylation signal; and
      (v) no structural gene encoding the EBNA-1 protein.

5. The method of claim 4 wherein said CHO cell is selected from the group consisting of CHO-DBX11 cells, CHO-K1 cells, CHO-DG44 cells, and CHO cells expressing EBNA-1.

6. A method for the production of a heterologous polypeptide comprising:
   a) culturing the CHO cell of claim 1 under conditions suitable for the expression of said heterologous polypeptide; and
   b) recovering said polypeptide from the culture.

7. The method of claim 6, wherein the heterologous polypeptide is selected from the group consisting of prodrugs, enzymes, enzyme fragments, enzyme inhibitors, enzyme activators, biologically active polypeptides, hedgehog proteins, bone morphogenetic proteins, growth factors, erythropoietin, thrombopoietin, G-CSF, interleukins, interferons, immunoglobulins, or immunoglobulin fragments.

8. The method of claim 7, wherein the heterologous polypeptide is an immunoglobulin or an immunoglobulin fragment.

9. A method for the expression and recovery of a heterologous polypeptide in a CHO cell, characterized in that said method comprises
   a) transfecting a CHO cell with an expression plasmid, wherein the CHO cell comprises a CHO cell stably transfected with the structural gene encoding the EBNA-1 protein and which does not contain the large T-antigen of Polyoma virus and wherein further the expression plasmid comprises
      (i) a single Epstein Barr Virus (EBV) derived element, wherein the single EBV derived element is an EBV origin of replication (oriP),
      (ii) no structural gene encoding the EBNA-1 protein,
      (iii) a prokaryotic origin of replication,
      (iv) a selection marker,
      (v) an expression cassette suitable for the expression of a heterologous polypeptide in said CHO cell, whereby said expression cassette comprises a promoter sequence, a 5' untranslated region, a nucleic acid sequence encoding said heterologous protein, and a 3' untranslated region comprising a polyadenylation signal;
   b) culturing said transfected cell under conditions suitable for the expression of said heterologous polypeptide; and
   c) recovering said heterologous polypeptide from the culture.

10. The method of claim 9 wherein said heterologous polypeptide is a secreted heterologous polypeptide.

11. The method of claim 9 wherein said culturing is carried out under transient transfection.

12. The method of claim 9 wherein said CHO cell is selected from the group consisting of CHO-DBX11 cells, CHO-K1 cells, CHO-DG44 cells, and CHO cells expressing EBNA-1.

13. A method for the production of a heterologous immunoglobulin, wherein said method comprises the following steps:
   a) cultivating a CHO cell under conditions suitable for the expression of said heterologous immunoglobulin, wherein the CHO cell
      (i) expresses the Epstein Barr Virus Nuclear Antigen 1 (EBNA-1);
      (ii) contains an episome, wherein said episome comprises
         (i) a prokaryotic origin of replication;
         (ii) a selection marker;
         (iii) a single Epstein Barr Virus (EBV) derived element, wherein the single EBV derived element is an EBV origin of replication (oriP);
         (iv) expression cassettes suitable for the expression of a heterologous immunoglobulin in said CHO cell, whereby said expression cassettes comprises a promoter sequence, a 5' untranslated region, a nucleic acid sequence encoding said heterologous immunoglobulin and a 3' untranslated region comprising a polyadenylation signal,
      wherein said episome does not contain a nucleic acid encoding EBNA-1; and
      (iii) does not contain the large T-antigen of Polyoma virus, and
   b) recovering said heterologous immunoglobulin from the culture.

* * * * *

SEQUENCE LISTING

<160> NUMBER OF SEQ ID NOS: 9

<210> SEQ ID NO 1
<211> LENGTH: 1998
<212> TYPE: DNA
<213> ORGANISM: Epstein Barr virus

<400> SEQUENCE: 1

```
gaattctatc attaaacggc atgcaggaaa aggacaagca gcgaaaattc acgccccctt      60
gggaggtggc ggcatatgca aaggatagca ctcccactct actactgggt atcatatgct     120
gactgtatat gcatgaggat agcatatgct acccggatac agattaggat agcatatact     180
acccagatat agattaggat agcatatgct acccagatat agattaggat agcctatgct     240
acccagatat aaattaggat agcatatact acccagatat agattaggat agcatatgct     300
acccagatat agattaggat agcctatgct acccagatat agattaggat agcatatgct     360
acccagatat agattaggat agcatatgct atccagatat ttgggtagta tatgctaccc     420
agatataaat taggatagca tatactaccc taatctctat taggatagca tatgctaccc     480
ggatacagat taggatagca tatactaccc agatatagat taggatagca tatgctaccc     540
agatatagat taggatagcc tatgctaccc agatataaat taggatagca tatactaccc     600
agatatagat taggatagca tatgctaccc agatatagat taggatagcc tatgctaccc     660
agatatagat taggatagca tatgctatcc agatatttgg gtagtatatg ctacccatgg     720
caacattagc ccaccgtgct ctcagcgacc tcgtgaatat gaggaccaac aaccctgtgc     780
ttggcgctca ggcgcaagtg tgtgtaattt gtcctccaga tcgcagcaat cgcgccccta     840
tcttggcccg cccacctact tatgcaggta ttccccgggg tgccattagt ggttttgtgg     900
gcaagtggtt tgaccgcagt ggttagcggg gttacaatca gccaagttat tacaccctta     960
ttttacagtc caaaaccgca gggcggcgtg tgggggctga cgcgtgcccc cactccacaa    1020
tttcaaaaaa aagagtggcc acttgtcttt gtttatgggc cccattggcg tggagccccg    1080
tttaattttc gggggtgtta gagacaacca gtggagtccg ctgctgtcgg cgtccactct    1140
ctttcccctt gttacaaata gagtgtaaca acatggttca cctgtcttgg tccctgcctg    1200
ggacacatct taataacccc agtatcatat tgcactagga ttatgtgttg cccatagcca    1260
taaattcgtg tgagatggac atccagtctt tacggcttgt ccccacccca tggatttcta    1320
ttgttaaaga tattcagaat gtttcattcc tacactagta tttattgccc aaggggtttg    1380
tgagggttat attggtgtca tagcacaatg ccaccactga acccccgtc caaattttat    1440 tctgggggcg tcacctgaaa ccttgttttc gagcacctca catacacctt actgttcaca    1500
actcagcagt tattctatta gctaaacgaa ggagaatgaa gaagcaggcg aagattcagg    1560
agagttcact gcccgctcct tgatcttcag ccactgccct tgtgactaaa atggttcact    1620
accctcgtgg aatcctgacc ccatgtaaat aaaaccgtga cagctcatgg ggtgggagat    1680
atcgctgttc cttaggaccc ttttactaac cctaattcga tagcatatgc ttcccgttgg    1740
```

```
gtaacatatg ctattgaatt agggttagtc tggatagtat atactactac ccgggaagca    1800
tatgctaccc gtttagggtt aacaaggggg ccttataaac actattgcta atgccctctt    1860
gagggtccgc ttatcggtag ctacacaggc ccctctgatt gacgttggtg tagcctcccg    1920
tagtcttcct gggcccctgg gaggtacatg tcccccagca ttggtgtaag agcttcagcc    1980
aagagttaca cataaagg                                                  1998

<210> SEQ ID NO 2
<211> LENGTH: 146
<212> TYPE: DNA
<213> ORGANISM: Epstein Barr virus

<400> SEQUENCE: 2
gatatcgctg ttccttagga ccctttact aaccctaatt cgatagcata tgcttcccgt      60
tgggtaacat atgctattga attagggtta gtctggatag tatatactac tacccgggaa    120
gcatatgcta cccgtttagg gttaac                                          146

<210> SEQ ID NO 3
<211> LENGTH: 622
<212> TYPE: DNA
<213> ORGANISM: Epstein Barr virus

<400> SEQUENCE: 3
gggtatcata tgctgactgt atatgcatga ggatagcata tgctacccgg atacagatta     60
ggatagcata tactacccag atatagatta ggatagcata tgctacccag atatagatta    120
ggatagccta tgctacccag atataaatta ggatagcata tactacccag atatagatta    180
ggatagcata tgctacccag atatagatta ggatagccta tgctacccag atatagatta    240
ggatagcata tgctacccag atatagatta ggatagcata tgctatccag atatttgggt    300
agtatatgct acccagatat aaattaggat agcatatact accctaatct ctattaggat    360
agcatatgct acccggatac agattaggat agcatatact acccagatat agattaggat    420
agcatatgct acccagatat agattaggat agcctatgct acccagatat aaattaggat    480
agcatatact acccagatat agattaggat agcatatgct acccagatat agattaggat    540
agcctatgct acccagatat agattaggat agcatatgct atccagatat ttgggtagta    600
tatgctaccc atggcaacat ta                                              622

<210> SEQ ID NO 4
<211> LENGTH: 1926
<212> TYPE: DNA
<213> ORGANISM: Epstein Barr virus

<400> SEQUENCE: 4
atgtctgacg aggggccagg tacaggacct ggaaatggcc taggagagaa gggagacaca     60
tctggaccag aaggctccgg cggcagtgga cctcaaagaa gaggggtga taaccatgga    120 cgaggacggg gaagaggacg aggacgagga ggcggaagac caggagcccc gggcggctca    180
ggatcagggc caagacatag atggtgtc cggagacccc aaaaacgtcc aagttgcatt      240
ggctgcaaag ggaccacgg tggaacagga gcaggagcag gagcgggagg ggcaggagca    300
ggaggggcag gagcaggagg aggggcagga gcaggaggag gggcaggagg ggcaggaggg    360
gcaggagggg caggagcagg aggaggggca ggagcaggag gagggcagg aggggcagga    420 ggggcaggag caggaggagg ggcaggagca ggagggggca ggagggggc aggagcagga    480 ggaggggcag gaggggcagg aggggcagga gcaggaggag gggcaggagc aggaggaggg    540
```

-continued

```
gcaggagggg caggagcagg aggaggggca ggaggggcag gaggggcagg agcaggagga    600
ggggcaggag caggaggggc aggaggggca ggaggggcag gagcaggagg ggcaggagca    660
ggaggagggg caggaggggc aggaggggca ggagcaggag gggcaggagc aggagggggca   720 ggagcaggag gggcaggagc aggaggggca ggaggggcag gagcaggagg ggcaggaggg    780
gcaggagcag gaggggcagg aggggcagga gcaggaggag gggcaggagg ggcaggagca    840
ggaggagggg caggaggggc aggagcagga ggggcaggag gggcaggagc aggaggggca    900
ggaggggcag gagcaggagg ggcaggaggg gcaggagcag gaggaggggc aggagcagga    960
ggggcaggag caggaggtgg aggccggggt cgaggaggca gtggaggccg ggtcgagga    1020 ggtagtggag gccggggtcg aggaggtagt ggaggccgcc ggggtagagg acgtgaaaga   1080 gccaggggg gaagtcgtga agagccagg gggagaggtc gtggacgtgg agaaaagagg    1140
cccaggagtc ccagtagtca gtcatcatca tccgggtctc caccgcgcag gccccctcca   1200
ggtagaaggc catttttcca ccctgtaggg aagccgatt attttgaata ccaccaagaa    1260
ggtggcccag atggtgagcc tgacgtgccc ccgggagcga tagagcaggg ccccgcagat    1320
gacccaggag aaggcccaag cactggaccc cggggtcagg gtgatggagg caggcgcaaa    1380
aaaggagggt ggtttggaaa gcatcgtggt caaggaggtt ccaacccgaa atttgagaac    1440
attgcagaag gtttaagagc tctcctggct aggagtcacg tagaaaggac taccgacgaa    1500
ggaacttggg tcgccggtgt gttcgtatat ggaggtagta agacctccct ttacaaccta    1560
aggcgaggaa ctgcccttgc tattccacaa tgtcgtctta caccattgag tcgtctcccc    1620
tttggaatgg cccctggacc cggcccacaa cctggcccgc taagggagtc cattgtctgt    1680
tatttcatgg tcttttaca aactcatata tttgctgagg ttttgaagga tgcgattaag    1740
gaccttgtta tgacaaagcc cgctcctacc tgcaatatca gggtgactgt gtgcagcttt    1800
gacgatggag tagatttgcc tccctggttt ccacctatgg tggaagggc tgccgcggag    1860 ggtgatgacg gagatgacgg agatgaagga ggtgatggag atgagggtga ggaagggcag    1920
gagtga                                                              1926
```

<210> SEQ ID NO 5
<211> LENGTH: 641
<212> TYPE: PRT
<213> ORGANISM: Epstein Barr virus

<400> SEQUENCE: 5

```
Met Ser Asp Glu Gly Pro Gly Thr Gly Pro Gly Asn Gly Leu Gly Glu
1               5                   10                  15

Lys Gly Asp Thr Ser Gly Pro Glu Gly Ser Gly Gly Ser Gly Pro Gln
            20                  25                  30

Arg Arg Gly Gly Asp Asn His Gly Arg Gly Arg Gly Arg Gly Arg Gly
        35                  40                  45

Arg Gly Gly Gly Arg Pro Gly Ala Pro Gly Gly Ser Gly Ser Gly Pro
    50                  55                  60

Arg His Arg Asp Gly Val Arg Arg Pro Gln Lys Arg Pro Ser Cys Ile
65                  70                  75                  80

Gly Cys Lys Gly Thr His Gly Gly Thr Gly Ala Gly Ala Gly Ala Gly
                85                  90                  95

Gly Ala Gly Ala Gly Gly Ala Gly Ala Gly Gly Ala Gly Ala Gly
            100                 105                 110

Gly Gly Ala Gly Gly Ala Gly Gly Ala Gly Gly Ala Gly Ala Gly Gly
```

```
            115                 120                 125
Gly Ala Gly Ala Gly Gly Ala Gly Ala Gly Gly Ala Gly Ala
        130                 135                 140
Gly Gly Gly Ala Gly Ala Gly Gly Ala Gly Ala Gly Ala Gly
145                 150                 155                 160
Gly Gly Ala Gly Gly Ala Gly Ala Gly Ala Gly Gly Ala Gly
            165                 170                 175
Ala Gly Gly Gly Ala Gly Gly Ala Gly Ala Gly Gly Ala Gly
        180                 185                 190
Ala Gly Gly Ala Gly Ala Gly Gly Ala Gly Ala Gly Gly Ala Gly
        195                 200                 205
Gly Ala Gly Gly Ala Gly Ala Gly Gly Ala Gly Ala Gly Gly Ala
        210                 215                 220
Gly Gly Ala Gly Gly Ala Gly Ala Gly Gly Ala Gly Ala Gly Ala
225                 230                 235                 240
Gly Ala Gly Gly Ala Gly Ala Gly Gly Ala Gly Gly Ala Gly
        245                 250                 255
Gly Ala Gly Gly Ala Gly Ala Gly Gly Ala Gly Ala Gly Ala Gly
        260                 265                 270
Gly Gly Ala Gly Gly Ala Gly Ala Gly Gly Gly Ala Gly Gly Ala Gly
        275                 280                 285
Ala Gly Gly Ala Gly Gly Ala Gly Ala Gly Gly Ala Gly Ala Gly
        290                 295                 300
Ala Gly Gly Ala Gly Gly Ala Gly Ala Gly Gly Ala Gly Ala Gly
305                 310                 315                 320
Gly Ala Gly Ala Gly Gly Gly Gly Arg Gly Arg Gly Gly Ser Gly Gly
            325                 330                 335
Arg Gly Arg Gly Gly Ser Gly Gly Arg Gly Arg Gly Gly Ser Gly Gly
        340                 345                 350
Arg Arg Gly Arg Gly Arg Glu Arg Ala Arg Gly Gly Ser Arg Glu Arg
        355                 360                 365
Ala Arg Gly Arg Gly Arg Gly Arg Gly Glu Lys Arg Pro Arg Ser Pro
        370                 375                 380
Ser Ser Gln Ser Ser Ser Gly Ser Pro Arg Arg Pro Pro Pro
385                 390                 395                 400
Gly Arg Arg Pro Phe Phe His Pro Val Gly Glu Ala Asp Tyr Phe Glu
            405                 410                 415
Tyr His Gln Glu Gly Gly Pro Asp Gly Glu Pro Asp Val Pro Pro Gly
        420                 425                 430
Ala Ile Glu Gln Gly Pro Ala Asp Asp Pro Gly Glu Gly Pro Ser Thr
        435                 440                 445
Gly Pro Arg Gly Gln Gly Asp Gly Gly Arg Arg Lys Lys Gly Gly Trp
450                 455                 460
Phe Gly Lys His Arg Gly Gln Gly Gly Ser Asn Pro Lys Phe Glu Asn
465                 470                 475                 480
Ile Ala Glu Gly Leu Arg Ala Leu Leu Ala Arg Ser His Val Glu Arg
            485                 490                 495
Thr Thr Asp Glu Gly Thr Trp Val Ala Gly Val Phe Val Tyr Gly Gly
        500                 505                 510
Ser Lys Thr Ser Leu Tyr Asn Leu Arg Arg Gly Thr Ala Leu Ala Ile
        515                 520                 525
```

```
Pro Gln Cys Arg Leu Thr Pro Leu Ser Arg Leu Pro Phe Gly Met Ala
    530                 535                 540

Pro Gly Pro Gly Pro Gln Pro Gly Pro Leu Arg Glu Ser Ile Val Cys
545                 550                 555                 560

Tyr Phe Met Val Phe Leu Gln Thr His Ile Phe Ala Glu Val Leu Lys
                565                 570                 575

Asp Ala Ile Lys Asp Leu Val Met Thr Lys Pro Ala Pro Thr Cys Asn
            580                 585                 590

Ile Arg Val Thr Val Cys Ser Phe Asp Asp Gly Val Asp Leu Pro Pro
        595                 600                 605

Trp Phe Pro Pro Met Val Glu Gly Ala Ala Ala Glu Gly Asp Asp Gly
    610                 615                 620

Asp Asp Gly Asp Glu Gly Gly Asp Gly Asp Glu Gly Glu Glu Gly Gln
625                 630                 635                 640

Glu

<210> SEQ ID NO 6
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgtttagtga accgtcagat cgcaaaaagc ttttttttaac acgta                45

<210> SEQ ID NO 7
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtgttaaaaa aagcttttttg cgatctgacg gttcactaaa cgagct            46

<210> SEQ ID NO 8
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ttttttaagc tttgccacca tgtctgacga ggggccaggt acag               44

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9 tttttttcact acgtgggtgc tggttgctcc cattcttagg tg                42
```